(12) United States Patent
Preiss-Bloom et al.

(10) Patent No.: US 10,869,954 B2
(45) Date of Patent: Dec. 22, 2020

(54) SURFACE TREATED BIOCOMPOSITE MATERIAL, MEDICAL IMPLANTS COMPRISING SAME AND METHODS OF TREATMENT THEREOF

(71) Applicants: Orahn Preiss-Bloom, Caesarea (IL); OSSIO LTD, Caesarea (IL)

(72) Inventors: Orahn Preiss-Bloom, Caesarea (IL); Taly Pnina Lindner, Caesarea (IL)

(73) Assignee: OSSIO, LTD., Caesarea (IL)

( * ) Notice: Subject to any disclaimer, the term of this patent is extended or adjusted under 35 U.S.C. 154(b) by 0 days.

(21) Appl. No.: 16/081,605

(22) PCT Filed: Mar. 7, 2017

(86) PCT No.: PCT/US2017/021103
§ 371 (c)(1),
(2) Date: Aug. 31, 2018

(87) PCT Pub. No.: WO2017/155956
PCT Pub. Date: Sep. 14, 2017

(65) Prior Publication Data
US 2019/0099522 A1    Apr. 4, 2019

Related U.S. Application Data

(60) Provisional application No. 62/304,689, filed on Mar. 7, 2016.

(51) Int. Cl.
*A61L 27/58*   (2006.01)
*A61L 27/46*   (2006.01)
(Continued)

(52) U.S. Cl.
CPC .............. *A61L 27/58* (2013.01); *A61L 27/46* (2013.01); *A61L 27/50* (2013.01); *A61L 31/127* (2013.01);
(Continued)

(58) Field of Classification Search
CPC ...... A61L 27/58; A61L 31/148; A61L 31/127; A61L 27/46; A61L 2430/02; A61L 2400/18; A61L 31/14; A61L 27/50
See application file for complete search history.

(56) References Cited

U.S. PATENT DOCUMENTS 4,655,777 A * 4/1987 Dunn ................... A61L 27/44
424/423
4,911,718 A   3/1990 Lee
(Continued)

FOREIGN PATENT DOCUMENTS

CN   1168105 A   12/1997
CN   1214939 A   4/1999
(Continued)

OTHER PUBLICATIONS

Arthrex Inc., "BioComposite Interference Screws—A Stronger turn in ACL/PCL Reconstruction", Scientific Research and Development, (20100000), URL: http://www.arthrex.com/knee/biocomposite-interference-screws. (6 pages).
(Continued)

*Primary Examiner* — Aradhana Sasan
*Assistant Examiner* — Quanglong N Truong
(74) *Attorney, Agent, or Firm* — Graeser Associates International, Inc.; Dvorah Graeser

(57) ABSTRACT

Reinforced biocomposite materials having a unique treated surface, in which the surface may comprise a plurality of layers. According to at least some embodiments, medical implants are provided that incorporate novel structures, alignments, orientations and forms comprised of such reinforced bioabsorbable materials, as well as methods of treatment thereof.

31 Claims, 22 Drawing Sheets

(51) Int. Cl.
   *A61L 31/12* (2006.01)
   *A61L 31/14* (2006.01)
   *A61L 27/50* (2006.01)

(52) U.S. Cl.
   CPC .............. *A61L 31/14* (2013.01); *A61L 31/148* (2013.01); *A61L 2400/18* (2013.01); *A61L 2430/02* (2013.01)

(56) References Cited

U.S. PATENT DOCUMENTS

| | | |
|---|---|---|
| 5,064,439 A | 11/1991 | Chang |
| 5,312,669 A | 5/1994 | Bedard |
| 5,338,772 A * | 8/1994 | Bauer .................... A61L 27/46 428/304.4 |
| 5,522,817 A | 6/1996 | Sander |
| 5,522,904 A | 6/1996 | Moran |
| 5,674,294 A | 10/1997 | Bainville |
| 6,004,650 A | 12/1999 | Schweizer |
| 6,299,649 B1 | 10/2001 | Chang |
| 6,471,707 B1 | 10/2002 | Miller |
| 6,511,511 B1 | 1/2003 | Slivka |
| 6,916,321 B2 | 7/2005 | Tenhuisen |
| 7,541,049 B1 | 6/2009 | Toermaelae Pertti |
| 7,918,879 B2 | 4/2011 | Yeung |
| 7,947,069 B2 | 5/2011 | Sanders |
| 8,702,716 B1 | 4/2014 | Stein |
| 8,992,622 B2 | 3/2015 | Ullrich, Jr. |
| 2005/0118326 A1 | 6/2005 | Anfinsen |
| 2005/0177245 A1 | 8/2005 | Leatherbury |
| 2005/0216016 A1 | 9/2005 | Contiliano |
| 2005/0226904 A1 | 10/2005 | Choi |
| 2005/0228500 A1 | 10/2005 | Kim |
| 2006/0020266 A1* | 1/2006 | Cooper ................. A61L 27/446 606/77 |
| 2006/0095134 A1 | 5/2006 | Trieu |
| 2006/0154206 A1 | 7/2006 | Petersson |
| 2006/0178748 A1* | 8/2006 | Dinger, III ......... A61B 17/1615 623/18.11 |
| 2007/0150059 A1 | 6/2007 | Ruberte |
| 2007/0185568 A1 | 8/2007 | Schwartz |
| 2007/0270969 A1 | 11/2007 | Schmid |
| 2007/0282455 A1 | 12/2007 | Luginbuehl |
| 2009/0112317 A1* | 4/2009 | Li ........................... A61L 27/24 623/16.11 |
| 2009/0240337 A1* | 9/2009 | Myung ................... A61L 27/34 623/18.11 |
| 2009/0304761 A1* | 12/2009 | Rabiei ................. A61C 8/0012 424/405 |
| 2010/0119564 A1 | 5/2010 | Kasuga |
| 2010/0168798 A1 | 7/2010 | Clineff |
| 2011/0098826 A1 | 4/2011 | Mauck |
| 2011/0166659 A1 | 7/2011 | Luginbuehl |
| 2012/0040015 A1 | 2/2012 | Lehtonen |
| 2012/0040137 A1 | 2/2012 | Palasis |
| 2012/0191214 A1* | 7/2012 | Nies ....................... A61L 27/40 623/23.62 |
| 2012/0265206 A1 | 10/2012 | Jang et al. |
| 2013/0144400 A1 | 6/2013 | Day |
| 2013/0218291 A1 | 8/2013 | Giorno |
| 2013/0317555 A1 | 11/2013 | Schaller |
| 2015/0238655 A1* | 8/2015 | Jongpaiboonkit ........................... A61K 38/1858 424/423 |
| 2015/0289979 A1 | 10/2015 | Gabele |

FOREIGN PATENT DOCUMENTS

| | | |
|---|---|---|
| CN | 1371664 A | 10/2002 |
| CN | 1565396 A | 1/2005 |
| CN | 1593356 A | 3/2005 |
| CN | 1953719 A | 4/2007 |
| CN | 101437467 A | 5/2009 |
| CN | 101790559 B | 7/2010 |
| CN | 102395329 A | 3/2012 |
| CN | 102421463 A | 4/2012 |
| EP | 1716874 A2 | 11/2006 |
| EP | 2292166 A1 | 3/2011 |
| EP | 3236866 | 11/2017 |
| JP | 6415040 | 1/1989 |
| JP | 2002501418 A | 1/2002 |
| JP | 2004160157 | 6/2004 |
| JP | 2008200510 | 9/2008 |
| JP | 2009541568 | 11/2009 |
| WO | 9819616 | 5/1998 |
| WO | 9819617 A1 | 5/1998 |
| WO | 9853768 | 12/1998 |
| WO | 9853768 A1 | 12/1998 |
| WO | 0132072 | 5/2001 |
| WO | 2005077039 A2 | 8/2005 |
| WO | 2005077039 A3 | 8/2005 |
| WO | WO-2005077039 A2 * | 8/2005 ......... A61B 17/7059 |
| WO | 2010122019 A1 | 10/2010 |
| WO | 2010122098 A2 | 10/2010 |
| WO | WO-2010122098 A2 * | 10/2010 ........... A61L 27/446 |
| WO | 2013116624 A1 | 8/2013 |
| WO | 2016035088 | 3/2016 |
| WO | 2016035088 A1 | 3/2016 |
| WO | 2016103049 | 6/2016 |
| WO | 2016103049 A1 | 6/2016 |
| WO | 2017155956 A1 | 9/2017 |

OTHER PUBLICATIONS

Australian Examination Report No. 1 for Application No. 2015310510, dated Aug. 10, 2019, 6 pages.
Chinese Office Action (with English language translation) for Application No. 201580036606.3, dated Mar. 12, 2019, 13 pages.
Chinese Office Action (with English language translation) for Application No. CN201580037255.8, dated Aug. 26, 2019, 16 pages.
Chinese Office Action (with English language translation) for Application No. CN201580070362.0, dated Aug. 29, 2019, 10 pages.
Chinese Office Action dated Jul. 13, 2018 for corresponding CN Patent Application No. 201580037255.8, 9 pages.
Chinese Office Action for Appl. No. 201580037255.8, dated Mar. 26, 2019, 7 pages.
European Search Report and Written Opinion dated Jun. 12, 2018 for EP Application No. 158720441, 5 pages.
European Search Report for EP15838477.6 dated Mar. 5, 2018, 5 pages.
IP Office of Singapore Written Opinion for Application No. SG11201610671P, dated Aug. 14, 2019, 5 pages.
Japanese Office Action (with English language translation) for Application No. 2017-504425, dated May 28, 2019, 7 pages.
Office Action dated Aug. 5, 2019 for U.S. Appl. No. 15/509,274 (pp. 1-19).
Scholz et al., "Composites Science and Technology", www.elsevier.com/locate/compscitech 71(2011) 1791-1803.
Search report for parent PCT application No. PCT/IL2015/050903, dated Jan. 7, 2016 (13 pages).
Supplementary European Search Report for EP15837823 dated Mar. 28, 2018, 6 pgs.
Wang et al., "Promising Poly(E-caprolactone) composite reinforced with weft-knitted polyester for small-diameter vascular graft application", Advances in Materials Science and Engineering, 2014, vol. 2014, p. 273891.
Wegener et al., "Microstructure, cytotoxicity and corrosion of powder-metallurgical iron alloys for biodegradable bone replacement materials", Materials Science & Engineering. B. Advanced Functional Solid-State Materials, 2011, vol. 176, No. 20, p. 1789-1796.
Australian Examination Report No. 1 for Application No. AU2015370600, dated Oct. 2, 2019, 3 pages.
Chinese Office Action (with English language translation) for Application No. CN201580036606.3, dated Oct. 25, 2019, 9 pages.

(56) References Cited

OTHER PUBLICATIONS

European Search Report dated Oct. 16, 2019 for EP Application No. 17763876.4, 11 pages.
International Search Report issued in PCT/IL2019/050843, dated Nov. 6, 2019, 3 pages.
Japanese Office Action (with English language translation) for Application No. JP2017-527796, dated Nov. 5, 2019, 6 pages.
Kulkova J. et al. "Hydroxyapatite and bioactive glass surfaces for fiber reinforced composite implants via surface ablation by Excimer laser" (2017) Journal of the Mechanical Behavior of Biomedical Materials, vol. 75, pp. 89-96, DOI: 10.1016/j.jmbbm.2017.07.005 (published on-line Jul. 4, 2017).
Office Action dated Nov. 7, 2019 for U.S. Appl. No. 15/523,389 (pp. 1-11).
Brazilian Search Report (with English language translation) for App No. BR112017001049-6, dated Apr. 8, 2020, 8 pages.
Brazilian Technical Report (with English language translation) for App No. BR112017012508-0, dated Apr. 8, 2020, 7 pages.
Chinese Office Action (with English language translation) for App No. CN201580070362.0, dated May 20, 2020, 9 pages.
Hyon et al., "Effects of Residual Monomer on the Degradation of DL-Lactide Polymer" Polymer International 46 (1998) 196-202.
Australian Examination Report No. 2 for Application No. AU2015310510, dated Dec. 1, 2019, 3 pages.
Australian Examination Report No. 2 for Application No. AU2015370600, dated Jan. 29, 2020, 2 pages.
Extended European Search Report for Application No. EP17819487.4, dated Feb. 4, 2020, 7 pages.
Extended European Search Report for Application No. EP19200585.8, dated Feb. 28, 2020, 8 pages.
Japanese Office Action (with English language translation) for Application No. JP2017-504425, dated Jan. 7, 2020, 6 pages.
Office Action dated Dec. 26, 2019 for U.S. Appl. No. 15/509,274, 18 pages.
Office Action dated Jan. 13, 2020 for U.S. Appl. No. 15/523,389 (pp. 1-11).
European Patent Office Communication pursuant to Article 94(3) EPC for App. No. EP17763876.4, dated Aug. 19, 2020, 9 pages.
Notice of Allowance dated Aug. 20, 2020 for U.S. Appl. No. 15/509,301 (pp. 1-9).

\* cited by examiner

SURFACE TREATED BIOCOMPOSITE MATERIAL, MEDICAL IMPLANTS COMPRISING SAME AND METHODS OF TREATMENT THEREOF

FIELD OF THE INVENTION

The present invention is of a surface treated biocomposite material, medical implants comprising same and methods of treatment thereof, and in particular to such material, implants and methods of treatment that have medical applications.

BACKGROUND OF THE INVENTION

The mechanical strength and modulus (approximately 3-5 GPa) of non-reinforced resorbable polymers is insufficient to support fractured cortical bone, which has an elastic modulus in the range of approximately 15-20 GPa. For example, in an article the bending modulus of human tibial bone was measured to be about 17.5 GPa (Snyder S M Schneider E, Journal of Orthopedic Research, Vol. 9, 1991, pp. 422-431). Therefore, the indications of existing medical implants constructed from resorbable polymers are limited and their fixation usually requires protection from motion or significant loading. These devices are currently only a consideration when fixation of low stress areas is needed (i.e. non-load bearing applications) such as in pediatric patients or in medial malleolar fractures, syndesmotic fixation, maxillofacial, or osteochondral fractures in adults.

A new class of reinforced composite biomaterials (biocomposites) has been recently introduced wherein a bioabsorbable and biocompatible polymer is reinforced by bioabsorbable, biocompatible glass fibers. These materials can achieve improved mechanical properties. These materials also involve a compatibilizer to bind the polymer to the reinforcing fibers. Examples of such materials are described in the following two patent applications, which are included fully herein by reference as if fully set forth herein:
1. Biocompatible composite and its use (WO2010122098)
2. Resorbable and biocompatible fibre glass compositions and their uses (WO2010122019)

These materials have been further described and characterized in publications associated with these patents including
1. Lehtonen T J et al. *Acta Biomaterialia* 9 (2013) 4868-4877
2. Lehtonen T J et al. *J Mech Behavior BioMed Materials.* 20 (2013) 376-386

The development of this class of materials described in the background art has focused on the composition of the materials: the bioabsorbable polymer, the reinforcing mineral fiber, the compatibilizer, and the combinations between them. These compositions have been demonstrated to be capable of achieving mechanical properties superior to the mechanical properties previously achieved with bioabsorbable polymers alone.

However, while material composition is one parameter that can affect mechanical properties of a medical implant, when it comes to composite materials, the material composition does not by itself ensure mechanical properties that are sufficient for the implant to achieve its desired biomechanical function. In fact, reinforced composite medical implants with identical compositions and identical geometries can have vastly different mechanical properties. Furthermore, even within the same implant, mechanical properties can vary greatly between different mechanical axes and between different types of mechanical strength measurements.

SUMMARY OF THE INVENTION

The background art does not teach or suggest biocomposite materials that have one or more desirable mechanical characteristics. The background art also does not teach or suggest such materials that can achieve a desired biomechanical function.

By "biocomposite material" it is meant a composite material that is biologically compatible or suitable, and/or which can be brought into contact with biological tissues and/or which can be implanted into biological materials and/or which will degrade, resorb or absorb following such implantation.

By "biocompatible" it is meant a material that is biologically compatible or suitable, and/or which can be brought into contact with biological tissues, and/or which can be implanted into biological materials.

By "surface treated" biocomposite material it is meant a material which features at least a surface layer, and optionally a plurality of surface layers.

The present invention, in at least some embodiments, relates to surface treated biocomposite materials which overcome the drawbacks of the background art. According to at least some embodiments, medical implants are provided that incorporate novel structures, alignments, orientations and forms comprised of such surface treated bioabsorbable materials.

The surface treated bioabsorbable materials are implemented as a biomedical implant, featuring a body composition and a surface layer, also described herein as a "surface". The body composition preferably features a combination of mineral and polymer, while the surface optionally features a different composition than the implant body. The surface may optionally comprise a plurality of surface layers, including at least one outer surface layer and at least one inner surface layer.

Optionally, 10-70% w/w of the body composition comprises mineral material. Also optionally, 30-55% w/w of the body composition comprises mineral material. Also optionally, 45-55% w/w of the body composition comprises mineral material.

Optionally, the polymer comprises PLDLA. Also optionally mineral material of said body composition comprises ranges of the following elements, all mol %: Na2O: 11.0-19.0, CaO: 9.0-14.0, MgO: 1.5-8.0, B2O3: 0.5-3.0, Al2O3: 0-0.8, P2O3: 0.1-0.8, SiO2: 67-73. Optionally, the mineral material of said body composition comprises ranges of the following elements, all mol %: Na2O: 12.0-13.0 mol. %, CaO: 9.0-10.0 mol. %, MgO: 7.0-8.0 mol. % B2O3: 1.4-2.0 mol. % P2O3: 0.5-0.8 mol. %, SiO2: 68-70 mol. %. Optionally, the mineral material of said body composition comprises ranges of the following elements, all mol %: Na2O: 11.0-19.0, CaO: 8.0-14.0, MgO: 2-8.0, B2O3: 1-3.0, Al2O3: 0-0.5, P2O3: 1-2, SiO2: 66-70% mol %.

The surface layer may optionally be implemented with a variety of different portions of the surface area having a different composition than the body composition. For example and without limitation, optionally more than 10% of an area of the surface is of a different composition than the body. Optionally more than 30% of the surface area is of a different composition than the body. Optionally more than 50% of the surface area is of a different composition than the body.

Optionally the body comprises an interspersed composition of mineral and polymer.

Optionally the surface layer may have various thicknesses, of which various non-limiting examples are given herein. For example, optionally the surface layer is defined as an outer layer of up to 100 micron depth. Optionally said outer layer is up to 50 micron depth. Optionally said outer layer is up to 20 micron depth. Optionally said outer layer is up to 5 micron depth. Optionally the surface layer is a uniform polymer or a bio composite composition different than the internal composition.

The surface layer may also optionally feature various concentrations of various materials. For example, optionally the surface layer of up to 5 microns includes an increase phosphate concentration. Optionally said outer layer features said increase in phosphate to more than 10% w/w. Optionally the outer layer includes an increase in calcium to more than five times the body composition. Optionally said increase in calcium is more than ten times the body composition. Optionally said increase in calcium is more than fifteen times the body composition.

Various surface layer structures are also optionally possible. For example, optionally said surface layer comprises a plurality of separate distinguished layers, each comprising a different composition.

Optionally the surface layer comprises at least an inner layer and an outer layer, wherein the outer layer is up to 3 microns and features an increase in phosphate to more than 5% w/w, wherein the inner layer is up to 20 microns and does not feature phosphate.

Optionally the treated portion of the surface layer has a roughness increase by more than five times the untreated surface. Optionally the treated portion of the surface layer has a roughness increase by more than ten times the untreated surface. Optionally the treated surface area increases the surface area by more than 15%. Optionally the treated surface area increases the surface area by more than 50%. Optionally the surface has a different mineral composition.

The body composition may also optionally feature various amounts of minerals and other ingredients. For example, optionally the body composition comprises more than 20% w/w mineral. Optionally the body composition comprises more than 40% w/w mineral.

Optionally said implant is cannulated, said surface layer comprises an inner surface layer and an outer surface layer, and an inner surface layer composition is different than an outer surface layer composition.

Optionally said implant is cannulated, said surface layer comprises an inner surface layer and an outer surface layer, and an inner surface layer composition is the same as an outer surface layer composition.

Optionally a surface of said implant is treated to partially expose inner composition.

Optionally the surface maximum roughness is more than 2 microns.

Optionally the surface maximum roughness is more than 3 microns.

Optionally said body composition comprises more than 8% w/w silica but said surface composition comprises less than 4% w/w silica.

Optionally the implant comprises a plurality of holes. Optionally said holes comprise an inner surface that is different from said surface of the implant. Optionally said inner surface comprises a different composition. Optionally said holes comprise an inner surface comprising a composition of said surface of the implant.

Optionally the body composition may be implemented as a plurality of reinforcing fibers, also as described herein.

These medical implants have unique mechanical properties. They have great clinical benefit in that these implants can have mechanical properties that are significant greater than those of the currently available bioabsorbable polymer implants. The term "mechanical properties" as described herein may optionally include one or more of elastic modulus, tensile modulus, compression modulus, shear modulus, bending moment, moment of inertia, bending strength, torsion strength, shear strength, impact strength, compressive strength and/or tensile strength.

Optionally any of the embodiments or sub-embodiments as described herein may be combined, for example in regard to any of the implant properties, implant structures or implant surface treatments, or any combination of any aspect of the same.

According to at least some embodiments, the implants have improved mechanical properties in at least one mechanical axis or parameter as compared with at least one other mechanical axis or parameter within the same implant. The implants can therefore be considered anisotropic. A mechanical axis as defined herein can be any line drawn through the implant, optionally passing through the center of the implant. A mechanical parameter as defined herein can include bending strength and stiffness (resistance to bending force), tensile strength and stiffness (resistance to tensile force), compression strength and stiffness (resistance to compression force), shearing strength and stiffness (resistance to shearing force), or torsional strength and stiffness (resistance to torsional force).

Optionally, the improved mechanical properties in one axis or parameter are increased by at least 500 as compared with another axis or parameter and are preferably increased by at least 100%, more preferably by at least 200%, 300%, 400%, and most preferably by at least 500% or any integral value in between.

Optionally, the improved mechanical properties in one axis or parameter of the implant are alternatively or additionally increased by at least 50% as compared with an implant of identical composition but with amorphous or non-aligned internal structure and are preferably increased by at least 100%, more preferably by at least 200%, 300%, 400%, and most preferably by at least 500% or any integral value in between.

Optionally, the improved mechanical property is strength and the strength in one axis or parameter is increased by at least 50 MPa as compared with another axis or parameter. Preferably, the strength is increased by at least 100 MPa, more preferably by at least 200 MPa, 300 MPa, 400 MPa, and most preferably by at least 500 MPa or any integral value in between.

Optionally, the improved mechanical property is strength and the strength in one axis or parameter of the implant is alternatively or additionally increased by at least 50 MPa as compared with an implant of identical composition but with amorphous or non-aligned internal structure, and preferably are increased by at least 100 MPa, more preferably by at least 200 MPa, 300 MPa, 400 MPa, and most preferably by at least 500 MPa or any integral value in between.

Optionally, the improved mechanical property is elastic modulus and the modulus in one axis or parameter is increased by at least 3 GPa as compared with another axis or parameter. Preferably, the modulus is increased by at least 5 GPa, more preferably by at least 8 GPa, 12 GPa, 16 GPa, and most preferably by at least 20 GPa or any integral value in between.

Optionally, the improved mechanical property is elastic modulus and the modulus in one axis or parameter of the implant is alternatively or additionally increased by at least 3 GPa as compared with an implant of identical composition but with amorphous or non-aligned internal structure. Preferably, the modulus is increased by at least 5 GPa, more preferably by at least 8 GPa, 12 GPa, 16 GPa, and most preferably by at least 20 GPa or any integral value in between.

According to at least some embodiments, anisotropocity of one or more segments of implant in one mechanical axis as compared with amorphous (non-aligned) material is preferably greater than 10%, 50%, 100%, 200%, 300%, 500% or any integral value in between.

According to at least some embodiments, anisotropocity of one or more segments of implant in one mechanical axis as compared with another axis is preferably greater than 10%, 50%, 100%, 200%, 500%, 1000% or any integral value in between.

According to at least some embodiments, there is provided relative higher strength in one mechanical axis as compared with another (e.g. bending over tensile) of 10%, 50%, 100%, 200%, 300% or any integral value in between.

According to at least some embodiments, there is provided relative higher elastic modulus as measured in one mechanical axis as compared with another of 10%, 30%, 50%, 100%, 200% or any integral value in between.

Without wishing to be limited by a closed list or a single hypothesis, the biocomposite implants described herein represent a significant benefit over metal or other permanent implants (including non absorbable polymer and reinforced polymer or composite implants) in that they are absorbable by the body of the subject receiving same, and thus the implant is expected to degrade in the body following implantation. Again without wishing to be limited by a closed list or a single hypothesis, they also represent a significant benefit over prior absorbable implants since they are stronger and stiffer than non-reinforced absorbable polymer implants in at least one mechanical axis. In fact, these reinforced composite polymer materials can even approach the strength and stiffness of cortical bone, making them the first absorbable materials for use in load bearing orthopedic implant applications.

On an underlying level, there is a great difference between the reinforced biocomposite implants and previous implants from metal, plastic, and other traditional medical implant materials. Traditional medical implant materials are isotropic such that their mechanical properties are identical in all axes. This simplifies implant design as the mechanical strength of the implant is determined solely based on the geometry of the implant and the inherent material properties of the material. Without wishing to be limited by a closed list or a single hypothesis, for reinforced biocomposite implants, the inherent material properties of the biocomposite (i.e. the biocomposite in amorphous or non-aligned form) are actually quite low and can approximate the mechanical properties of the polymer alone. As such, implant geometries for implants constructed from these biocomposite materials does not inherently determine implants that are mechanically strong or stiff.

However, the medical implants of the present invention in at least some embodiments are able to exceed the mechanical properties of previous bioabsorbable implants, including previous biocomposite implants in one or more mechanical axes and in one or more mechanical parameters. Preferably these implants feature structures and forms in which the reinforcing fibers are aligned within the implant in order to provide the implant load bearing strength and stiffness in the axes in which these properties are biomechanically required. Thus, either the entire implant or segments of the implant are anisotropic (i.e. they have different mechanical properties in different axes). With these anisotropic implants, the implant mechanical design cannot rely solely on the geometry of each part. Rather, the specific alignment of the reinforcing fibers within the implant and the resulting anisotropic mechanical profile are a key parameter in determining the biomechanical function of the implant.

Aside from the mechanical considerations related to the anisotropic medical implants, there are additional limitations in that medical implants using these reinforced biocomposite materials cannot be designed according to existing implant designs due to the limitations associated with producing parts from these composite materials.

For example, metal implants or permanent polymer implants may be produced by machining. Even fiber-reinforced permanent polymer implants may be machined without adversely affecting the mechanical properties. However, absorbable, reinforced composite material implants cannot be machined without causing damage to the underlying material since machining will expose reinforcing fibers from the polymer, thus causing their strength to degrade quickly once they are directly exposed to body fluid following implantation.

At the other end of the spectrum, pure polymer or very short (<4 mm) fiber-reinforced polymer implants may be manufactured using straightforward injection molding processes. Injection molding of these materials does not, however, result in sufficiently strong implants. Therefore, specialized designs and production methods are required in order to design and produce an implant that can benefit from the superior mechanical properties of the previously described reinforced bioabsorbable composite materials.

The term "biodegradable" as used herein also refers to materials that are degradable, resorbable or absorbable in the body.

The term "load bearing" optionally also includes partially load bearing. According to various embodiments, the load bearing nature of the device (implant) may optionally include flexural strengths above 200 MPa, preferably above 300 MPa, more preferably above 400 MPa, 500 MPa. and most preferably above 600 MPa or any integral value in between.

The biocomposite orthopedic implants as described herein feature a composite of mineral compositions and bioabsorbable polymer. Optionally, a majority or entirety of the surface of the implant is comprised of the bioabsorbable polymer. This may result from the underlying composition of the biocomposite or from the production method (such as injection or compression molding) used to produce the implant. However, the attachment and incorporation of bone to the mineral composition component of the implant is generally better than the attachment of bone to the polymer. This may be due to one or more factors including the relative hydrophilicity of the mineral component as compared with the polymer component, increased porosity of the mineral component as compared with the polymer component, or additional factors.

Therefore, in order to improve the attachment of bone to a biocomposite implant, according to at least some embodiments of the present invention, there is provided such an implant in which the percentage of the implant surface that is comprised of mineral component is maximized. Optionally and preferably, such maximization is implemented by introducing roughness or porosity to the surface of the biocomposite implant to further improve the bone attachment to the biocomposite implant.

It should be noted that such maximization may optionally be implemented with any biocomposite implant featuring a combination of mineral compositions and bioabsorbable polymer, and not only such implants as described herein.

Unless otherwise defined, all technical and scientific terms used herein have the same meaning as commonly understood by one of ordinary skill in the art to which this invention belongs. The materials, methods, and examples provided herein are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3A shows a sample with majority of layers with fiber orientation perpendicular to implant longitudinal axis. FIG. 3B shows a sample with majority of layers with fiber orientation parallel to implant longitudinal axis;

FIG. 5A shows an amorphous fiber orientation sample; FIG. 5B shows a sample with majority of layers with fiber orientation perpendicular to implant longitudinal axis. FIG. 5C shows a sample with majority of layers with fiber orientation parallel to implant longitudinal axis;

FIG. 8A is a photo of the pin along its length; FIG. 8B is a photo of the cross-section of the pin;

FIG. 9A is a photo of the pin along its length; FIG. 9B is a photo of the cross-section of the pin.

FIG. 11A shows force distribution on a hollow cylinder pin implant with a wall thickness made of 5 layers as demonstrated in FIG. 11B.

DETAILED DESCRIPTION OF SOME EMBODIMENTS

Figure 1C:
FIG. 1 shows some exemplary plates according to at least some embodiments of the present invention.

A medical implant according to at least some embodiments of the present invention is suitable for load-bearing orthopedic implant applications and comprises one or more bioabsorbable materials where sustained mechanical strength and stiffness are critical for proper implant function.

According to at least some embodiments of the present invention, there is provided orthopedic implants, such as those for bone fixation, made from reinforced bioabsorbable composite materials. Specifically, implants according to at least some embodiments incorporate characteristics, features, or properties that can either only be achieved using the reinforced bioabsorbable composite materials or are specifically advantageous for implants comprised of these types of materials, or optionally a combination of both in a single implant.

Surface and Body Compositions

According to at least some embodiments, the reinforced biocomposite medical implant is comprised of an internal composition region, or "body," and a surface region, defined as the region comprising the surface layer of part or all of the implant.

The surface region may be further broken down into an outermost (external) surface region and innermost (internal) surface region, each of which may have different properties.

The surface region may cover the entire surface of the implant but can also cover only a percentage of the surface of the implant, with the remaining surface being of the same properties as the internal composition region. Preferably, surface region covers at least a majority of the entire surface of the implant.

Optionally, one or more cannulation or screw hole voids may be present on the inside of implant, which may or may not be included in the calculation of implant surface.

Surface region can be defined as a layer of average depth in the range of 0.1-200 micron, preferably 1-100 micron, more preferably 2-75 micron and most preferably 5-50 micron.

Outermost surface region can be defined as the external layer of the surface region with an average depth in the range of 0.1-100 micron, preferably 0.5-50 micron, more preferably 1-25 micron and most preferably 1-10 micron.

In one embodiment, the implant is a mineral fiber-reinforced biocomposite implant and fewer reinforcing fibers are present in either the entire surface region or the outermost surface region as compared with the internal composition region. Preferably, fiber to polymer weight composition ration in surface region is less than 50% of fiber to polymer weight ratio in internal composition region. More preferably less than 30%, and most preferably less than 10%. Optionally, no fibers are present in surface region or the outermost surface region.

In one embodiment, outermost surface region has been modified to increase roughness and/or porosity.

Optionally roughness is defined by presence of promontories, prominences or protuberances on the surface of the implant with height equal to or less than the depth of the outermost surface region. Preferably such promontories, prominences or protuberances are less than 5 microns in diameter, on average. More preferably, less than 3, less than 2, less than 1 micron in average diameter. Optionally such promontories, prominences or protuberances are present in the outermost surface area but absent in the innermost surface area.

Optionally roughness is defined by Ra measure in nanometers (nm). Preferably roughness in modified outermost surface area is greater than 100 nm, more preferably greater than 200 nm, and most preferably greater than 300 nm. Preferably roughness in unmodified surface area is less than 100 nm.

Optionally, porosity is defined as full thickness pore (holes) in the entire surface region or outermost surface layer. Preferably, implant is a mineral fiber-reinforced implant and porosity in surface layer exposes mineral fibers.

Optionally, the surface region has lower mineral content than the internal composition region.

Optionally, the internal composition region has:
Sodium (Na) weight composition of 1-10%, preferably 2-8%, and more preferably 3-6%.
Magnesium (Mg) weight composition of 0.4-1.5%, preferably 0.4-1.2%, and more preferably 0.8-1.2%.
Silica (Si) weight composition of 1-20%, preferably 5-15%, and more preferably 9-13%.
Phosphorous (P) weight composition of less than 3%, preferably less than 1%.
Calcium (Ca) weight composition of 1-20%, preferably 1-10%, preferably 1-3%.

Optionally, the innermost surface region has lower mineral content than internal composition region.

Optionally, the innermost surface region has:
Sodium (Na) weight composition of less than 1.9%, preferably less than 1.5%. Preferably the sodium weight composition of innermost surface region is 50% less than sodium weight composition of internal composition and more preferably 30% less.
Magnesium (Mg) weight composition of less than 0.3%, preferably less than 0.2%. Preferably the magnesium weight composition of innermost surface region is 50% less than magnesium weight composition of internal composition and more preferably 30% less.
Silica (Si) weight composition of less than 6%, preferably less than 4%. Preferably silica weight composition of innermost surface region is 50% less than silica weight composition of internal composition and more preferably 30% less.
Phosphorous (P) weight composition of less than 3%, preferably less than 1%.
Calcium (Ca) weight composition of less than 1%, preferably less than 0.5%. Preferably calcium weight composition of innermost surface region is 50% less than calcium weight composition of internal composition and more preferably 30% less.

Optionally, the outermost surface region has higher mineral content than the innermost surface region.

Optionally, outermost surface region has:
Sodium (Na) weight composition of less than 1.9%, preferably less than 1.5%.
Magnesium (Mg) weight composition of less than 1%, preferably less than 0.5%. Preferably magnesium weight composition of outermost surface region is greater than magnesium weight composition of innermost surface region.
Silica (Si) weight composition of less than 6%, preferably less than 4%. Preferably silica weight composition of outermost surface region is 50% less than silica weight composition of internal composition and more preferably 30% less.
Phosphorous (P) weight composition in range of 1-15%, preferably 3-13%. Preferably phosphorous weight composition of outermost surface region is at least 50% greater than phosphorous weight composition of innermost layer or than internal composition or than both; more preferably at least 70% greater and most preferably at least 90% greater.

Calcium (Ca) weight composition in range of 15-50%, preferably 15-30%. Preferably calcium weight composition of outermost surface region is at least 100% greater than calcium weight composition of innermost layer, more preferably at least 500% greater and most preferably at least 1000% greater.

Biocomposite Implants with Modified Surface Area

According to at least some embodiments, there is provided a biocomposite medical implant with a modified surface wherein the outermost surface layer of the implant is comprised of a majority of bioabsorbable polymer but wherein the surface has been modified such that the surface of the implant comprises roughness, texture, or porosity such that an increased amount of mineral composition is exposed as compared with the outermost surface layer of the implant.

Outermost surface layer as used herein may define the outermost 1-100 µm of the implant. Preferably the outermost 1-20 µm of the implant, more preferable the outermost 1-10, and most preferably the outer 1-5.

The exposed mineral composition may comprise the mineral composition that is part of the biocomposite composition. The mineral composition may optionally or additionally comprise another mineral such as Hydroxyapatite, Calcium Phosphate, Calcium Sulfate, Dicalcium Phosphate, Tricalcium Phosphate.

The roughness or texture of the surface may include exposure of the internal composition of the implant to a depth of the outermost 1-100 µm of the implant. Preferably the outermost 1-20 µm of the implant, more preferable the outermost 1-10, and most preferably the outer 1-5 microns.

Preferably, the outermost layer of the implant comprises at least 30% polymer, more preferably at least 50%, more preferably at least 70%, and most preferably at least 80%.

The composition of the biocomposite is comprised of at least 20% mineral composition, preferably at least 30%, more preferably at least 40%, and most preferably at least 50%.

Preferably the composition of the outermost layer of the implant comprises a greater percentage of polymer than the overall composition of the implant. Preferably, at least 10% more, 20%, 30%, 50%

Optionally, the modified surface of the implant includes pores in the polymer surface. The average pore diameter is preferably in the range of 1-500 µm, more preferably in the range 10-300 µm, more preferably in the range 50-250 µm.

Preferably, surface is modified with surface treatment using grit blasting.

Preferably grit is comprised of a biocompatible material.

Preferably grit is comprised of a combination of Hydroxyapatite, Calcium Phosphate, Calcium Sulfate, Dicalcium Phosphate, and Tricalcium Phosphate.

Preferably grit is of an average diameter size in the range of 10-500 µm. More preferably in the range of 20-120 µm.

Bioabsorbable Polymers

In a preferred embodiment of the present invention, the biodegradable composite comprises a bioabsorbable polymer.

The medical implant described herein may be made from any biodegradable polymer. The biodegradable polymer may be a homopolymer or a copolymer, including random copolymer, block copolymer, or graft copolymer. The biodegradable polymer may be a linear polymer, a branched polymer, or a dendrimer. The biodegradable polymers may be of natural or synthetic origin. Examples of suitable biodegradable polymers include, but are not limited to polymers such as those made from lactide, glycolide, caprolactone, valerolactone, carbonates (e.g., trimethylene carbonate, tetramethylene carbonate, and the like), dioxanones (e.g., 1,4-dioxanone), δ-valerolactone, 1,dioxepanones) e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, poly (ortho esters), hydroxy alkanoates, tyrosine carbonates, polyimide carbonates, polyimino carbonates such as poly (bisphenol A-iminocarbonate) and poly (hydroquinone-iminocarbonate, (polyurethanes, polyanhydrides, polymer drugs (e.g., polydiflunisol, polyaspirin, and protein therapeutics (and copolymers and combinations thereof. Suitable natural biodegradable polymers include those made from collagen, chitin, chitosan, cellulose, poly (amino acids), polysaccharides, hyaluronic acid, gut, copolymers and derivatives and combinations thereof.

According to the present invention, the biodegradable polymer may be a copolymer or terpolymer, for example: polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, such as lactide/tetramethylglycolide copolymers, lactide/trimethylene carbonate copolymers, lactide/d-valerolactone copolymers, lactide/ε-caprolactone copolymers, L-lactide/DL-lactide copolymers, glycolide/L-lactide copolymers (PGA/PLLA), polylactide-co-glycolide; terpolymers of PLA, such as lactide/glycolide/trimethylene carbonate terpolymers, lactide/glycolide/ε-caprolactone terpolymers, PLA/polyethylene oxide copolymers; polydepsipeptides; unsymmetrically—3, 6-substituted poly-1,4-dioxane-2,5-diones; polyhydroxyalkanoates; such as polyhydroxybutyrates (PHB); PHB/b-hydroxyvalerate copolymers (PHB/PHV); poly-b-hydroxypropionate (PHPA); poly-p-dioxanone (PDS); poly-d-valerolactone-poly-ε-caprolactone, poly(ε-caprolactone-DL-lactide) copolymers; methylmethacrylate-N-vinyl pyrrolidone copolymers; polyesteramides; polyesters of oxalic acid; polydihydropyrans; polyalkyl-2-cyanoacrylates; polyurethanes (PU); polyvinylalcohol (PVA); polypeptides; poly-b-malic acid (PMLA): poly-b-alkanbic acids; polycarbonates; polyorthoesters; polyphosphates; poly(ester anhydrides); and mixtures thereof; and natural polymers, such as sugars; starch, cellulose and cellulose derivatives, polysaccharides, collagen, chitosan, fibrin, hyaluronic acid, polypeptides and proteins. Mixtures of any of the above-mentioned polymers and their various forms may also be used.

The biodegradable composite is preferably embodied in a polymer matrix, which may optionally comprise any of the above polymers. Optionally and preferably, it may comprise a polymer selected from the group consisting of a bioabsorbable polyester, PLLA (poly-L-lactide), PDLLA (poly-DL-lactide), PLDLA, PGA (poly-glycolic acid), PLGA (poly-lactide-glycolic acid), PCL (Polycaprolactone), PLLA-PCL and a combination thereof. If PLLA is used, the matrix preferably comprises at least 30% PLLA, more preferably 50%, and most preferably at least 70% PLLA. If PDLA is used, the matrix preferably comprises at least 5% PDLA, more preferably at least 10%, most preferably at least 20% PDLA.

Optionally, the inherent viscosity (IV) of the polymer matrix (independent of the reinforcement fiber) is in the range of 0.2-6 dl/g, preferably 1.0 to 3.0 dl/g, more preferably in the range of 1.5 to 2.4 dl/g, and most preferably in the range of 1.6 to 2.0 dl/g.

Inherent Viscosity (IV) is a viscometric method for measuring molecular size. IV is based on the flow time of a polymer solution through a narrow capillary relative to the flow time of the pure solvent through the capillary.

Reinforced Biocomposite

According to at least some embodiments of the present invention, the medical implant comprises a reinforced biocomposite (i.e. a bioabsorbable composite that includes the previously described polymer and also incorporates a reinforcing filler, generally in fiber form, to increase the mechanical strength of the polymer). For the avoidance of doubt, the terms "filler" and "fiber" are used interchangeably to describe the reinforcing material structure.

In a more preferred embodiment of the present invention, the reinforced bioabsorbable polymer is a reinforced polymer composition comprised of any of the above-mentioned bioabsorbable polymers and a reinforcing filler, preferably in fiber form. The reinforcing filler may be comprised of organic or inorganic (that is, natural or synthetic) material. Reinforcing filler may be a biodegradable glass or glass-like materials, a ceramic, a mineral composition (optionally including one or more of hydroxyapatite, tricalcium phosphate, calcium sulfate, calcium phosphate), a cellulosic material, a nano-diamond, or any other filler known in the art to increase the mechanical properties of a bioabsorbable polymer. The filler may also optionally be a fiber of a bioabsorbable polymer itself. Preferably, reinforcing fiber is comprised of a bioabsorbable glass, ceramic, or mineral composition.

Preferably, reinforcement fiber is comprised of silica-based mineral compound such that reinforcement fiber comprises a bioresorbable glass fiber, which can also be termed a bioglass fiber composite.

According to at least some embodiments, bioresorbable glass fiber may optionally have oxide compositions in the following mol. % ranges (as a percent over the glass fiber composition):

$Na_2O$: 11.0-19.0 mol. %
CaO: 9.0-14.0 mol. %
MgO: 1.5-8.0 mol. %
$B_2O_3$: 0.5-3.0 mol. %
$Al_2O_3$: 0-0.8 mol. %
$P_2O_3$: 0.1-0.8 mol. %
$SiO_2$: 67-73 mol. %
but preferably in the following mol. % ranges:
$Na_2O$: 12.0-13.0 mol. %
CaO: 9.0-10.0 mol. %
MgO: 7.0-8.0 mol. %
$B_2O_3$: 1.4-2.0 mol. %
$P_2O_3$: 0.5-0.8 mol. %
$SiO_2$: 68-70 mol. %

Additional optional bioresorbable glass compositions are described in the following patent applications, which are hereby incorporated by reference as if fully set forth herein: Biocompatible composite and its use (WO2010122098); and Resorbable and biocompatible fibre glass compositions and their uses (WO2010122019).

Tensile strength of the reinforcement fiber is preferably in the range of 1200-2800 MPa, more preferably in the range of 1600-2400 MPa, and most preferably in the range of 1800-2200 MPa.

Elastic modulus of the reinforcement fiber is preferably in the range of 30-100 GPa, more preferably in the range of 50-80 GPa, and most preferably in the range of 60-70 GPa.

Reinforcing filler is preferably incorporated in the bioabsorbable polymer matrix of the biocomposite in fiber form. Preferably, such fibers are continuous fibers.

Preferably continuous fibers are aligned within the implant such that the ends of fibers don't open at the surface of the implant.

Preferably, fibers are distributed evenly within the implant.

Specifically within bioabsorbable fiber-reinforced composites, achieving the high strengths and stiffness required for many medical implant applications can require the use of continuous-fiber reinforcement rather than short or long fiber reinforcement. This creates a significant difference from the implant structures, architectures, designs, and production techniques that have been previously used with medical implants produced from polymers or composites comprising short or long fiber reinforced polymers. Those implants are most commonly produced using injection molding, or occasionally 3-D printing, production techniques. The production of these implants generally involves homogeneity of the material throughout the implant and the finished implant is then comprised of predominantly isotropic material. However, with continuous fiber-reinforcement, the fibers must be carefully aligned such that each fiber or bundle of fibers runs along a path within the composite material such that they will provide reinforcement along specific axes within the implant to provide stress resistance where it is most needed.

The present invention provides, in at least some embodiments, implant compositions from continuous-fiber reinforced bioabsorbable composite materials that are a significant step forward from previous bioabsorbable implants in that they can achieve sustainably high, load bearing strengths and stiffness. Additionally, many embodiments of the present invention additionally facilitate these high strength levels with efficient implants of low volume since the anisotropic nature of the implants can allow the implants to achieve high mechanical properties in axes where those properties are needed (for example in bending resistance) without necessitating the additional volume that would be needed to uniformly provide high mechanical properties in all other axes.

According to at least some embodiments, there is provided a medical implant comprising a plurality of composite layers, said layers comprising a biodegradable polymer and a plurality of uni-directionally aligned continuous reinforcement fibers. Optionally and preferably, the biodegradable polymer is embodied in a biodegradable composite. Also optionally and preferably, the fibers are embedded in a polymer matrix comprising one or more bioabsorbable polymers.

According to at least some embodiments, the composite layers are each comprised of one or more composite tapes, said tape comprising a biodegradable polymer and a plurality of uni-directionally aligned continuous reinforcement fibers. Optionally and preferably, the biodegradable polymer is embodied in a biodegradable composite. Also optionally and preferably, the fibers are embedded in a polymer matrix comprising one or more bioabsorbable polymers.

Preferably, the composite tape layer comprises reinforcement fibers that are pre-impregnated with polymer.

Preferably, each composite layer is of thickness 0.05 mm-0.5 mm, more preferably 0.15-0.35 mm, and most preferably 0.1-0.25 mm.

Preferably, each composite tape is of width 2-30 mm, more preferably tape is of width 4-16 mm, and most preferably of width 6-12 mm.

Preferably, reinforcement fiber content within the composite tape is in the range of 20-70%, more preferably in the range of 30-60%, more preferably in the range of 40-50%, and most preferably 45-50% over the entire composite tape materials.

Optionally and preferably, the fiber-reinforced biodegradable composite within the implant has a flexural modulus exceeding 10 GPa and flexural strength exceeding 100 MPa.

Optionally, the fiber-reinforced biodegradable composite within the implant has flexural strength in range of 200-1000 MPa, preferably 300-800 MPa, more preferably in the range of 400-800 MPa, and most preferably in the range of 500-800 MPa Optionally, the fiber-reinforced biodegradable composite within the implant has elastic modulus in range of 10-30 GPa, preferably 12-28 GPa, more preferably in the range of 16-28 GPa, and most preferably in the range of 20-26 GPa.

Optionally, fibers may be aligned at an angle to the longitudinal axis (i.e. on a diagonal) such that the length of the fiber may be greater than 100% of the length of the implant. Optionally and preferably, a majority of reinforcement fibers are aligned at an angle that is less than 90°, alternatively less than 60°, or optionally less than 45° from the longitudinal axis.

Preferably, the implant preferably comprises between 2-20 composite tape layers, more preferably between 2-10 layers, and most preferably between 2-6 layers; wherein each layer may be aligned in a different direction or some of the layers may be aligned in the same direction as the other layers.

Preferably, the maximum angle between fibers in at least some of the layers is greater than the angle between the fibers in each layer and the longitudinal axis. For example, one layer of reinforcing fibers may be aligned and a right diagonal to the longitudinal axis while another layer may be aligned at a left diagonal to the longitudinal axis.

Optionally and preferably, the composite composition additionally includes a compatibilizer, which for example be such an agent as described in WO2010122098, hereby incorporated by reference as if fully set forth herein.

Reinforcing fiber diameter preferably in range of 2-40 um, preferably 8-20 um, most preferably 12-18 um (microns).

Preferably, the implant includes only one composition of reinforcing fiber.

Preferably fibers don't open at the surface of the implant.

Numerous examples of reinforced polymer compositions have previously been documented. For example: A biocompatible and resorbable melt derived glass composition where glass fibers can be embedded in a continuous polymer matrix (EP 2 243 749 A1), Biodegradable composite comprising a biodegradable polymer and 20-70 vol % glass fibers (WO2010128039 A1), Resorbable and biocompatible fiber glass that can be embedded in polymer matrix (US 2012/0040002 A1), Biocompatible composite and its use (US 2012/0040015 A1), Absorbable polymer containing poly[succinimide] as a filler (EP0 671 177 B1).

In a more preferred embodiment of the present invention, the reinforcing filler is covalently bound to the bioabsorbable polymer such that the reinforcing effect is maintained for an extended period. Such an approach has been described in US 2012/0040002 A1 and EP 2243500B1, hereby incorporated by reference as if fully forth herein, which discusses a composite material comprising biocompatible glass, a biocompatible matrix polymer and a coupling agent capable of forming covalent bonds.

Fabrication of the Implant

Any of the above-described bioabsorbable polymers or reinforced bioabsorbable polymers may be fabricated into any desired physical form for use with the present invention. The polymeric substrate may be fabricated for example, by compression molding, casting, injection molding, pultrusion, extrusion, filament winding, composite flow molding (CFM), machining, or any other fabrication technique known to those skilled in the art. The polymer may be made into any shape, such as, for example, a plate, screw, nail, fiber, sheet, rod, staple, clip, needle, tube, foam, or any other configuration suitable for a medical device.

Load-Bearing Mechanical Strength

The present invention particularly relates to bioabsorbable composite materials that can be used in medical applications that require high strength and a stiffness compared to the stiffness of bone. These medical applications require the medical implant to bear all or part of the load applied by or to the body and can therefore be referred to generally as "load-bearing" applications. These include bone fixation, fracture fixation, tendon reattachment, joint replacement, spinal fixation, and spinal cages.

The flexural strength preferred from a bioabsorbable composite (such as a reinforced bioabsorbable polymer) for use in the load-bearing medical implant is at least 200 MPa, preferably above 400 MPa, more preferably above 600 MPa, and even more preferably above 800 MPa. The Elastic Modulus (or Young's Modulus) of the bioabsorbable composite for use with present invention is preferably at least 10 GPa, more preferably above 15 GPa, and even more preferably above 20 GPa but not exceeding 100 GPa and preferably not exceeding 60 GPa.

Sustained Mechanical Strength

There is a need for the bioabsorbable load-bearing medical implants of the present invention to maintain their mechanical properties (high strength and stiffness) for an extended period to allow for sufficient bone healing. The strength and stiffness preferably remains above the strength and stiffness of cortical bone, approximately 150-250 MPa and 15-25 GPa respectively, for a period of at least 3 months, preferably at least 6 months, and even more preferably for at least 9 months in vivo (i.e. in a physiological environment).

More preferably, the flexural strength remains above 400 MPa and even more preferably remains above 600 MPa.

The present invention overcomes the limitations of previous approaches and provides medical implants comprised of biodegradable compositions that retain their high mechanical strength and stiffness for an extended period sufficient to fully support bone regeneration and rehabilitation.

"Biodegradable" as used herein is a generalized term that includes materials, for example polymers, which break down due to degradation with dispersion in vivo. The decrease in mass of the biodegradable material within the body may be the result of a passive process, which is catalyzed by the physicochemical conditions (e.g. humidity, pH value) within the host tissue. In a preferred embodiment of biodegradable, the decrease in mass of the biodegradable material within the body may also be eliminated through natural pathways either because of simple filtration of degradation by-products or after the material's metabolism ("Bioresorption" or "Bioabsorption"). In either case, the decrease in mass may result in a partial or total elimination of the initial foreign material. In a preferred embodiment, said biodegradable composite comprises a biodegradable polymer that undergoes a chain cleavage due to macromolecular degradation in an aqueous environment.

A polymer is "absorbable" as described herein if it is capable of breaking down into small, non-toxic segments which can be metabolized or eliminated from the body without harm. Generally, absorbable polymers swell, hydrolyze, and degrade upon exposure to bodily tissue, resulting in a significant weight loss. The hydrolysis reaction may be enzymatically catalyzed in some cases. Complete bioabsorption, i.e. complete weight loss, may take some time, although preferably complete bioabsorption occurs within 24 months, most preferably within 12 months.

The term "polymer degradation" means a decrease in the molecular weight of the respective polymer. With respect to the polymers, which are preferably used within the scope of the present invention said degradation is induced by free water due to the cleavage of ester bonds. The degradation of the polymers as for example used in the biomaterial as described in the examples follows the principle of bulk erosion.

Thereby a continuous decrease in molecular weight precedes a highly pronounced mass loss. Such loss of mass is attributed to the solubility of the degradation products. Methods for determination of water induced polymer degradation are well known in the art such as titration of the degradation products, viscometry, differential scanning calorimetry (DSC).

Bulk degradation refers to a process of degradation in which there is at least some perfusion of fluid through the material that is being degraded, such as the body of the implant, thereby potentially degrading the bulk of the material of the implant (as opposed to the external surface alone). This process has many effects. Without wishing to be limited to a closed list, such bulk degradation means that simply making an implant larger or thicker may not result in improved retained strength.

Surface degradation refers to a process of degradation in which the external surface undergoes degradation. However, if there is little or no perfusion of fluid through the material that is being degraded, then the portion of the implant that is not on the surface is expected to have improved retained strength over implants in which such perfusion occurs or occurs more extensively.

Material Specific Design Benefits

Without wishing to be limited by a closed list, the material-specific design benefits are optionally provided by one or more of the following unique characteristics of implants manufactured from this material:

1. Absorbable structural implants wherein strength and stiffness properties are anisotropic. The bending resistance and other mechanical properties of these implants depends greatly on the specific design of the part and of the alignment of reinforcing fibers within the part. It is therefore possible to design such implants efficiently such that they provide sufficient support in the necessary axes (for example, flexural stiffness) without comprising an excessive amount of material that would provide equivalent support in the remaining axes (for example, tensile stiffness).

2. Low profile/minimally invasive/material efficient design for absorbable implant that take advantage of the strength and stiffness characteristics of the reinforced absorbable composite material to create implants that achieve bone fixation with minimal profile. By "minimal profile", it is meant that the implant is reduced in size in at least one dimension in comparison with an equivalent currently available implant that is not made from such composite material.

3. Load bearing absorbable bone implants, as opposed to previous absorbable implants which did not approach the stiffness of cortical bone.

4. Small functional features, such as anchors, ridges, teeth, etc that require the reinforcement in order to be strong enough to be functional. Previous absorbable materials may not have had sufficient strength for such features.

5. The capability of being produced according to fiber-reinforced composite specific manufacturing techniques such as compression molding, pultrusion, etc.

6. Reduced damage to surrounding tissues, including both soft tissues and bone tissues, as compared with the trauma of stress risers or stress shielding that can arise from use of high modulus (such as metal) implants.

The present invention, according to at least some embodiments, thus provides medical implants that are useful as structural fixation for load-bearing purposes, exhibiting sustained mechanical properties.

The present invention, according to at least some embodiments, further comprises a biodegradable composite material in which the drawbacks of the prior art materials can be minimized or even eliminated, i.e. the composite retains its strength and modulus in vivo for a time period sufficient for bone healing for example. Mechanical strength as used here includes, but is not limited to, bending strength, torsion strength, impact strength, compressive strength and tensile strength.

The presently claimed invention, in at least some embodiments, relate to a biocomposite material comprising a biocompatible polymer and a plurality of reinforcing fibers, wherein said reinforcing fibers are oriented in a parallel orientation.

The biocomposite material has one or more mechanical properties which feature an increased extent or degree as compared to such a material with reinforcing fibers oriented in a non-parallel orientation. Optionally such a non-parallel orientation is a perpendicular or amorphous (non-oriented) orientation. elastic modulus, tensile modulus, compression modulus, shear modulus, bending moment, moment of inertia, bending strength, torsion strength, shear strength, impact strength, compressive strength and/or tensile strength. The increased extent or degree may optionally be at least twice as great, at least five times as great, at least ten times as great, at least twenty times as great, at least fifty times as great, or at least a hundred times as much, or any integral value in between.

Optionally the mechanical properties can comprise any one of Flexural strength, Elastic modulus and Maximum load, any pair of same or all of them. Optionally density and/or volume are unchanged or are similar within 5%, within 10%, within 15%, within 20%, any integral value in between or any integral value up to 50%.

Optionally the biocomposite implant as described herein is swellable, having at least 0.5% swellability, at least 1%, 2% swellability, and less than 20% swellability, preferably less than 10% or any integral value in between.

Optionally, the swellability in one mechanical axis is greater than the swellability in a second mechanical axis. Preferably the difference in swelling percentage (%) between axes is at least 10%, at least 25%, at least 50%, or at least 100%, or any integral value in between.

After exposure to biological conditions for 1 hour, 12 hours, 24 hours, 48 hours, five days, one week, one month, two months or six months or any time value in between, the biocomposite material implants preferably retain at least 10%, at least 20%, at least 50%, at least 60%, at least 75%, at least 85% or up to 100% of flexural strength, Modulus and/or Max load, and/or volume, or any integral value in between. By "biological conditions" it is meant that the temperature is between 30-40 C but preferably is at 37 C.

Optionally, fluid conditions replicate those in the body as well, under "simulated body fluid" conditions.

The flexural strength of the implant or segment of the implant is preferably at least 200 MPA, at least 400 mPa, at least 600 mPA, at least 1000 mPA or any integral value in between.

Relevant implants may include bone fixation plates, intramedullary nails, joint (hip, knee, elbow) implants, spine implants, and other devices for such applications such as for fracture fixation, tendon reattachment, spinal fixation, and spinal cages.

According to at least some embodiments, there are provided medical implants for bone or soft tissue fixation comprising a biodegradable composite, wherein said composite optionally and preferably has the following properties:

(i) wherein biodegradable composite comprises one or more biodegradable polymers and a resorbable, reinforcement fiber; and (ii) wherein one or more segments comprising the medical implant have a maximum flexural modulus in the range of 6 GPa to 30 GPa and flexural strength in the range of 100 MPa to 1000 MPa; and (iii) wherein the average density of the composite is in the range of 1.1-3.0 g/cm$^3$.

Preferably, average density of the composite is in the range of 1.2-2.0 g/cm$^3$.

More preferably, average density of the composite is in the range of 1.3-1.6 g/cm$^3$.

Preferably, flexural modulus is in the range of 10 GPa to 28 GPa and more preferably in the range of 15 to 25 GPa.

Preferably, flexural strength is in the range of 200-800 MPa. More preferably, 400-800 MPa.

In a preferred embodiment of the present invention, at least 50% of elastic modulus is retained following exposure to simulated body fluid (SBF) at 50° C. for 3 days. More preferably at least 70% is retained, and even more preferably at least 80% is retained.

In a preferred embodiment of the present invention, at least 20% of strength is retained following exposure to simulated body fluid (SBF) at 50° C. for 3 days. More preferably at least 30% is retained, and even more preferably at least 40% is retained.

In a preferred embodiment of the present invention, at least 50% of elastic modulus is retained following exposure to simulated body fluid (SBF) at 37° C. for 3 days. More preferably at least 70%, and even more preferably at least 85%.

In a preferred embodiment of the present invention, at least 30% of strength is retained following exposure to simulated body fluid (SBF) at 37° C. for 3 days. More preferably at least 45%, and even more preferably at least 60%.

Specifically regarding medical implants described herein that contain one or more segments that can be anisotropic, this anisotropicity reflects a significant divergence from what has be previously accepted in medical, and specifically orthopedic, implants in that the anisotropic structure results in implants in which there are mechanical properties in one or more axis that are less than the optimal mechanical properties which may be achieved by the materials from which the implant is comprised. In contrast, traditional implants have relied upon the uniform mechanical properties of the materials from which they are comprised as this does not require compromising in any axis.

The anisotropic approach can only be applied following biomechanical analysis to determine that greater implant mechanical properties is required in certain axes as opposed to other axes. For example, an implant may be subjected to very high bending forces but only nominal tensile forces and therefore require a much greater emphasis on bending forces. Other relevant axes of force in a medical implant can include tensile, compression, bending, torsion, shear, pull-out (from bone) force, etc.

There are several factors that affect the mechanical properties of an implant. As described above, material composition alone results in a generally uniform or isotropic structure. Without wishing to be limited by a closed list or a single hypothesis, within fiber-reinforced biocomposite medical implants, an anisotropic structure may result from one or more of the following characteristics:

1. The weight ratio of reinforcing fibers to biopolymer. Preferably this ratio is in the range of 1:1 to 3:1 and more preferably 1.5:1 to 2.5:1.
2. The density of the medical implant (this characteristic is also determined to some extent the ratio of reinforcing fiber to polymer)
3. The diameter of reinforcing fiber. The average fiber diameter is preferably between 5 and 50 µm. More preferably between 10-30 µm.
4. Length of fiber (continuous fiber, long fiber, short fiber). Preferably, having continuous fiber reinforcement with fibers that run across the entire implant.
5. The alignment of fibers or fiber layers. Preferably, in each segment of the implant, a majority of fibers or fiber layers are aligned or partially aligned with the axis that will be exposed to the highest bending forces. If partially aligned, then preferably within a 45° angle of the axis.
6. The number of fibers or fiber layers aligned in any given direction. Preferably fiber layers are 0.1 to 1 mm in thickness and more preferably 0.15 to 0.25 mm.
7. The order of fiber layers.

In one embodiment of the present invention, the medical implant is a pin, screw, or wire.

Preferably, a pin or wire of 2 mm external diameter will have a shear load carrying capacity of greater than 200 N. More preferably shear load carrying capacity of 2 mm pin will exceed 400 N and most preferably will exceed 600 N.

Clinical Applications

The medical implants discussed herein are generally used for bone fracture reduction and fixation to restore anatomical relationships. Such fixation optionally and preferably includes one or more, and more preferably all, of stable fixation, preservation of blood supply to the bone and surrounding soft tissue, and early, active mobilization of the part and patient.

There are several exemplary, illustrative, non-limiting types of bone fixation implants for which the materials and concepts described according to at least some embodiments of the present invention may be relevant, as follows:

Screws

Screws are used for internal bone fixation and there are different designs based on the type of fracture and how the screw will be used. Screws come in different sizes for use with bones of different sizes. Screws can be used alone to hold a fracture, as well as with plates, rods, or nails. After the bone heals, screws may be either left in place or removed.

Screws are threaded, though threading can be either complete or partial. Screws can include compression screws, locking screws, and/or cannulated screws. External screw diameter can be as small as 0.5 or 1.0 mm but is generally less than 3.0 mm for smaller bone fixation. Larger bone cortical screws can be up to 5.0 mm and cancellous screws can even reach 7-8 mm. Some screws are self-tapping and others require drilling prior to insertion of the screw. For cannulated screws, a hollow section in the middle is generally larger than 1 mm diameter in order to accommodate guide wires.

Wires/Pins

Wires are often used to pin bones back together. They are often used to hold together pieces of bone that are too small to be fixed with screws. They can be used in conjunction with other forms of internal fixation, but they can be used alone to treat fractures of small bones, such as those found in the hand or foot. Wires or pins may have sharp points on either one side or both sides for insertion or drilling into the bone.

"K-wire" is a particular type of wire generally made from stainless steel, titanium, or nitinol and of dimensions in the range of 0.5-2.0 mm diameter and 2-25 cm length. "Steinman pins" are general in the range of 2.0-5.0 mm diameter and 2-25 cm length. Nonetheless, the terms pin and wire for bone fixation are used herein interchangeably.

Anchors

Anchors and particularly suture anchors are fixation devices for fixing tendons and ligaments to bone. They are comprised of an anchor mechanism, which is inserted into the bone, and one or more eyelets, holes or loops in the anchor through which the suture passes. This links the anchor to the suture. The anchor which is inserted into the bone may be a screw mechanism or an interference mechanism. Anchors are generally in the range of 1.0-6.5 mm diameter Cable, Ties, Wire Ties Cables, ties, or wire ties (one example of wire tie is Synthes ZipFix™) can be used to perform fixation by cerclage, or binding, bones together. Such implants may optionally hold together bone that cannot be fixated using penetration screws or wires/pin, either due to bone damage or presence of implant shaft within bone. Generally, diameter of such cable or tie implants is optionally in the range of 1.0 mm-2.0 mm and preferably in the range of 1.25-1.75 mm. Wire tie width may optionally be in the range of 1-10 mm.

Nails or Rods

In some fractures of the long bones, medical best practice is to hold the bone pieces together is through insertion of a rod or nail through the hollow center of the bone that normally contains some marrow. Screws at each end of the rod are used to keep the fracture from shortening or rotating, and also hold the rod in place until the fracture has healed. Rods and screws may be left in the bone after healing is complete. Nails or rods for bone fixation are generally 20-50 cm in length and 5-20 mm in diameter (preferably 9-16 mm). A hollow section in the middle of nail or rod is generally larger than 1 mm diameter in order to accommodate guide wires.

Other non-limiting, illustrative examples of bone fixation implants may optionally include plates, plate and screw systems, and external fixators.

Any of the above-described bone fixation implants may optionally be used to fixate various fracture types including but not limited to comminuted fractures, segmental fractures, non-union fractures, fractures with bone loss, proximal and distal fractures, diaphyseal fractures, osteotomy sites, etc.

Bending Resistance

The primary mechanical challenge to wires or pins used for bone fixation is providing mechanical support (i.e. bending resistance) under bending/flexural stress to prevent the stress from creating a gap between the bone surfaces in the fracture which can prevent good bone healing. For absorbable bone fixation implants, it is desirable for the implant to provide bending resistance such that the implant deflects a similar amount or less than the bones which it is fixating when exposed to bending stress. It is further desirable for the implant to provide this bending resistance with the minimal profile (i.e. minimal amount of material) in order to minimize the amount of degradation products over time and also to reduce implant cost.

For a wire or pin, the amount of deflection it undergoes when subjected to a flexural stress is directly related to (i) the flexural modulus of the material of which the implant is made; and (ii) the second moment of inertia of the cross-section of the wire or pin across the axis across which the flexural stress is being applied.

Second moment of inertia refers to the property of a shape that directly correlates to its ability to resist bending and deflection. Second moment of inertia can alternatively be referred to as second moment of area, moment of inertia of plane area, area moment of inertia, polar moment of area or second area moment.

In a preferred embodiment of the present invention, the elastic modulus of the implant or a segment of the implant as measured with flexural/bending testing is greater than the elastic modulus of the implant or a segment of the implant as measured with tensile testing. Preferably, the difference is greater than 5%, more preferred the difference is greater than 10%, even more preferred greater than 20%, 30%, 40%, 50%.

In a preferred embodiment of the present invention, the flexural/bending strength of the implant is greater than its tensile or compressive strength. In a more preferred embodiment, this difference is greater than 5%. Even more preferred, the higher flexural/bending strength as compared with tensile or compressive strength is greater by at least 10%, 30%, 50%, 70%, and most preferably 100%.

In an optional embodiment, the anisotropic nature of the medical implants described according to at least some embodiments of the present invention result in the mechanical properties in the bending axis that are superior to the mechanical properties in the tensile or compressive axis. This difference can be at least partially determined by the alignment, orientation, or structure of reinforcing fibers with the bioabsorbable polymer matrix, as described in more detail above.

In a hollow tube geometry, its flexural/bending stiffness is relatively greater than its tensile stiffness. The flexural stiffness is relative to the second moment of inertia around the axis of bending, for example the second moment of inertia around the midline axis of a square pin/beam is $I_x = bh^3/12$ and for a hollow circular pin/beam, $I_x = \pi(do^4 - di^4)/64$. Conversely, the tensile stiffness is relative to the cross-sectional area, $A = bh$ for a square pin/beam and $A = \pi(do^2 - di^2)/4$ for a hollow circular pin/beam.

In a preferred embodiment of the present invention, one or more voids are present within the implant, such that the second moment of inertia of the cross-section of the wire or pin across the mid-line axis of the implant is less than the second moment of inertia for such a part with the same or similar external dimensions but a void-less (i.e. whole or solid) cross-sectional area. Preferably, the reduction in the second moment of inertia is smaller than 30%, more preferably 20% and most preferably 10% than for a solid part.

Alternatively, a wire or pin may comprise open space between different struts, ribs, arms, etc of the wire or pin such that wire or pin forms an asterisk type cross-section thereby similarly providing increased relative flexural stiffness in relation to its tensile stiffness.

Preferably, the average cross-sectional area of the wire or pin is reduced by a greater percentage than the average second moment of inertia of its cross-section as compared to a solid part with similar dimensions as previously described. More preferably, the cross-sectional area is more than 20% smaller while the second moment of inertia is reduced by less than 20%. Even more preferably, the cross-sectional area is more than 20% smaller while the second moment of inertia is reduced by less than 10%.

Dimensions

For orthopedic implants, it is desirable for the implant to have a minimal profile so as to allow for implantation with minimal soft tissue damage. Furthermore, it is preferable to produce the implant with sufficient robustness to provide necessary mechanical strength but otherwise not contain extraneous material.

In a preferred embodiment of the present invention, the external diameter of the wire or pin is less than 15 mm, more preferably less than 10 mm, even more preferably less than 5 mm and most preferably less than 3 mm.

In a preferred embodiment of the present invention, the wall thickness of the wire or pin is less than 5 mm, more preferably less than 3 mm, even more preferably less than 1 mm and most preferably less than 0.7 mm.

Voids in Implant

As described above, it may be desirable to have a wire or pin that is hollow in order to provide bending resistance with the most efficient amount of material. Nonetheless, there are potential complications involved in implanting a hollow implant in bone, as non-bone tissue cells, such as fibroblasts, can penetrate into the hollow void and thereby impede or slow regeneration of bone in that area.

In a preferred embodiment of the present invention, the wire or pin contains a hollow section or void internally but such void is covered such that cells cannot invade void prior to degradation of implant material.

In another embodiment of the present invention, the hollow section can be filled with active ingredients such as antibiotics, growth factors or bone filler to prevent such invasion.

In another embodiment hollow section can be used to introduce active ingredients into fracture area via holes in the wall of the hollow wire or pin.

Example #1

The below example describes the extent to which the anisotropic nature of the herein described reinforced bio-composite implants impacts the mechanical properties of the implants. Depending on the mechanical property parameter, the differences in the degree of anisotropicity in a medical implant or medical implant part can reach even 5× or greater. Without wishing to be limited by a single hypothesis, these differences may be due to differences between alignments of reinforcing fibers within the implant.

Materials and Methods

Rectangular testing samples (dimensions 50.8 mm×12.7 mm×1 mm), simulating plates used for small bone fixation, were produced using reinforced composite material. Material composite was comprised of PLDLA 70/30 polymer reinforced with 40%-50% w/w continuous mineral fibers. Mineral fibers were as described for composition "NX-8" in Lehtonen T J et al. *Acta Biomaterialia* 9 (2013) 4868-4877. Mineral composition was specifically approximately $Na_2O$ 14%, MgO 5.4%, CaO 9%, $B_2O_3$ 2.3%, $P_2O_5$ 1.5%, and $SiO_2$ 67.8% w/w. All testing samples were from one plate, manufactured by compression molding of five layers of composite material, each comprised of the PLDLA polymer with embedded uni-directionally aligned continuous fibers. Each layer was 0.18 mm thick.

In four samples, orientation of layers relative to longitudinal axis of implant were 0° (parallel to implant longitudinal axis), 45°, 0°, −45°, 0°. In four other samples, orientation of layers relative to longitudinal axis were 90° (perpendicular to implant longitudinal axis), −45°, 90°, 45°, 90°.

Implant samples were tested for Flexural strength, Elastic modulus and Maximum load according to ASTM D790-10 with a 500N load cell and a 3 point bending fixture (220Q1125-95, TestResources, MN, USA). Load span was 25.4 mm and cross head speed was set at 1.092 mm/min. Dimensions, weight and density of samples were measured. Statistical comparison between two treatments was performed using a t-test. A confidence level of p=0.05 was used.

Results

Figure 2:
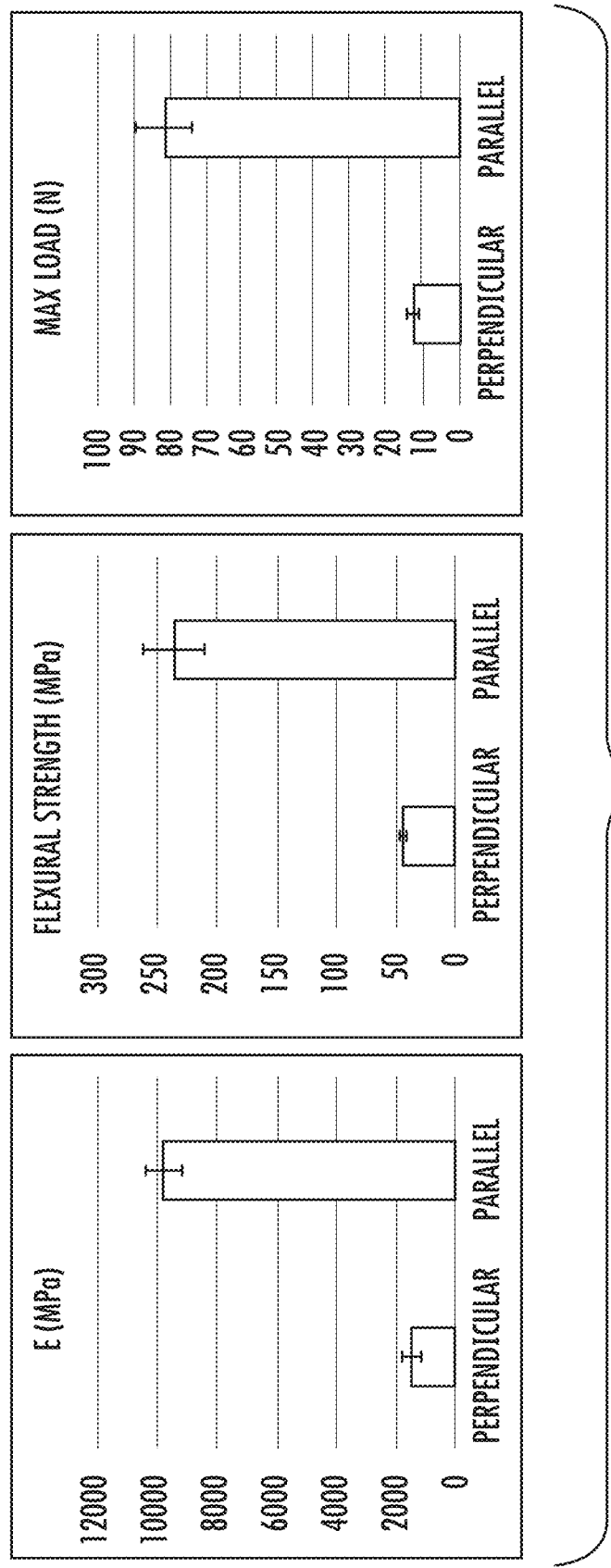
FIG. 2 shows the anisotropic properties of a bio-composite plate as demonstrated by the large difference in mechanical properties of samples with identical compositions, but with a majority of layers aligned at either 0° (Parallel) or 90° (Perpendicular) to the longitudinal axis of the implant sample (n=4)

FIG. 2 shows the anisotropic properties of a bio-composite plate as demonstrated by the large difference in mechanical properties of samples with identical compositions, but with a majority of layers aligned at either 0° (Parallel) or 90° (Perpendicular) to the longitudinal axis of the implant sample (n=4). The numerical results are summarized in Table 1.

TABLE 1

Mean values and standard deviations of statistically significant mechanical properties of the anisotropic implants, (n = 4). Density and Volume of the different samples were similar.

| | E [MPa] | Flexural Strength [MPa] | Max Load [N] | Density [gr/ml] | Volume [mm³] |
|---|---|---|---|---|---|
| Perpendicular | 1524.4 ± 281 | 45.9 ± 1.6 | 12.4 ± 1.4 | 1.48 ± 0.01 | 662.1 ± 32.3 |
| Parallel | 9795.4 ± 610 | 235.4 ± 25.4 | 81.4 ± 7.7 | 1.49 ± 0.03 | 694.0 ± 19.3 |
| Anisotropicity [%] [Par/perp*100] | 642.6 | 512.8 | 656.3 | | |

Figure 3A:
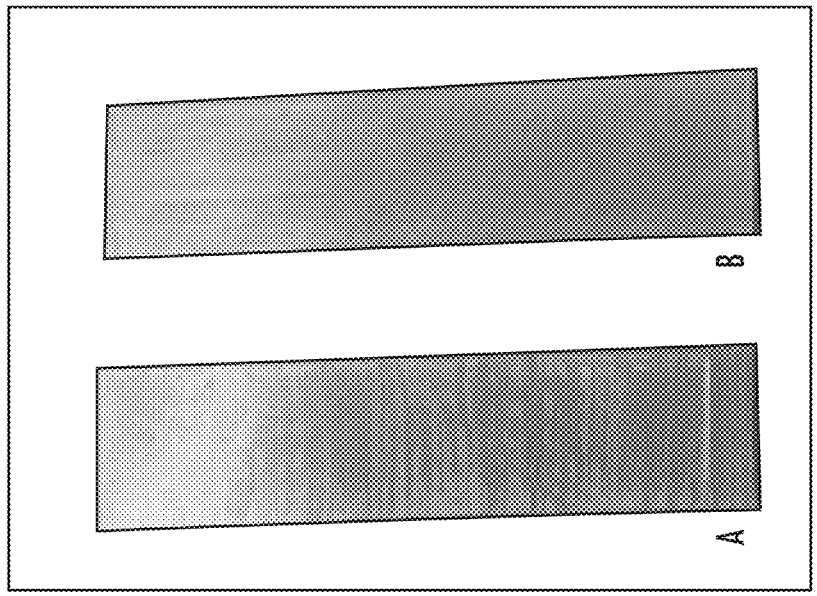
FIGS. 3A and 3B show representative examples of samples.
Figure 3B:
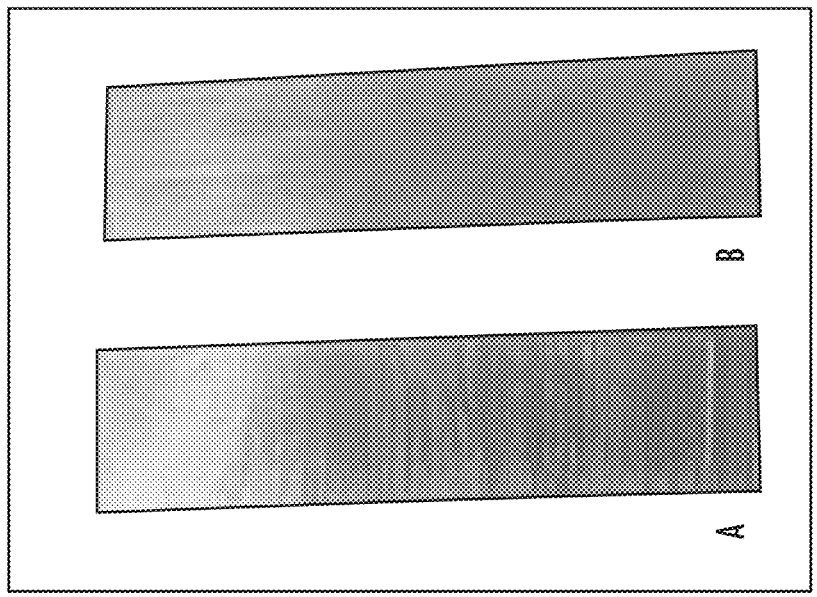

FIG. 3 shows representative examples of samples. FIG. 3A shows a sample with majority of layers with fiber orientation perpendicular to implant longitudinal axis. FIG. 3B shows a sample with majority of layers with fiber orientation parallel to implant longitudinal axis. The mechanical properties of sample B were superior to those of sample A. Anisotropicity of mechanical properties in this example was more than 500%. The anisotropocity was calculated as a percentage by dividing each of the mechanical parameter values as measured for the samples with perpendicular (transverse) fiber alignment by the corresponding value as measured for the samples with parallel fiber alignment.

Example #2

The below example describes the extent to which the anisotropic nature of the herein described reinforced biocomposite implants impacts the mechanical properties of the implants. This example additionally shows that an implant comprised of a randomly distributed, or amorphous, composition of reinforced biocomposite materials will have far inferior mechanical properties in the desired axis to the herein described anisotropic medical implant with alignment of reinforcing fibers that maximizes the mechanical properties in the desired axis (in this case, bending force).

The example also demonstrates anisotropicity in that the modulus, when measured by flexural testing, can be either higher or lower than the tensile modulus of the same part depending on the directionality of the flexural test.

Materials and Methods

Rectangular testing samples (dimensions 50.8 mm×12.7 mm×0.7 mm), simulating plates used for small bone fixation, were produced using reinforced composite material. Material composite was as described in Example 1.

16 testing samples were produced, manufactured by compression molding of four layers of composite material. Each layer was 0.18 mm thick. In four samples, samples were each comprised of the PLDLA polymer with embedded uni-directionally aligned continuous fibers where orientation of layers relative to longitudinal axis of implant were 0° (parallel to implant longitudinal axis), 0°, 0°, 0°. In four other samples, orientation of layers relative to longitudinal axis were 90° (perpendicular to implant longitudinal axis), 90°, 90°, 90°. In four other samples, the continuous fiber embedded layers were not uni-directionally aligned but rather the layers were chopped into segments of approximately 3 mm and then molded together into the rectangular plates in bulk. In other words, the composition of these last four samples was identical to that of the continuous fiber groups but the material was used with random alignment, hereafter referred to as an "amorphous" form.

12 implant samples were tested for Flexural strength, Elastic modulus and Maximum load according to ASTM D790-10 with a 500N load cell and a 3 point bending fixture (220Q1125-95, TestResources, MN, USA). Load span was 25.4 mm and cross head speed was set at 1.47 mm/min (1.71 mm/min for amorphous plates due to thinner dimension). Dimensions, weight and density of samples were measured.

4 implant samples (n=4) were tested for tensile strength, tensile modulus and maximum load according to modified ASTM D3039M with a 5 KN load cell and an appropriate fixture (220Q1125-95, TestResources, MN, USA). Sample span was 30 mm at the beginning of the test and cross head speed was set at 2 mm/min. Dimensions, weight and density of samples were recorded.

Results

Figure 4:
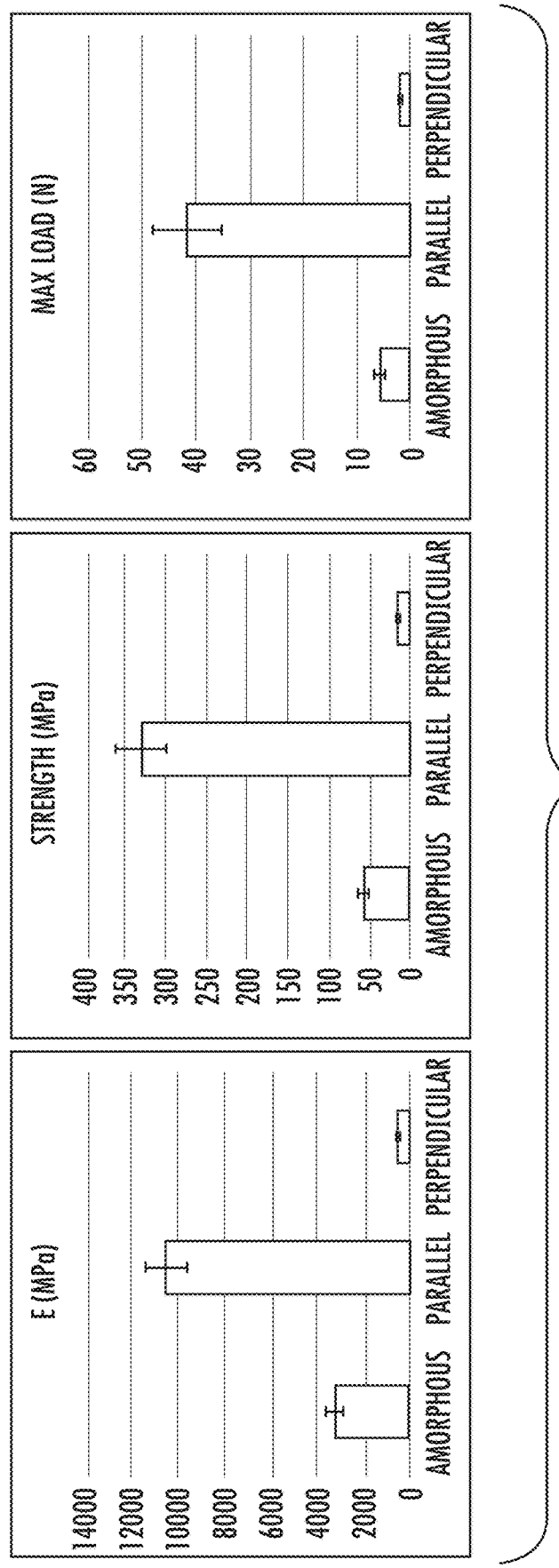
FIG. 4 shows that the anisotropic properties of a bio-composite plate are directly affected by fiber orientation, as demonstrated by the large difference in mechanical properties of samples with identical compositions, but with non-aligned layers (Amorphous) or with layers aligned at either 0° (Parallel) or 90° (Perpendicular) to the longitudinal axis of the implant sample (n=4)

FIG. 4 shows that the anisotropic properties of a biocomposite plate are directly affected by fiber orientation, as demonstrated by the large difference in mechanical properties of samples with identical compositions, but with non-aligned layers (Amorphous) or with layers aligned at either 0° (Parallel) or 90° (Perpendicular) to the longitudinal axis of the implant sample (n=4). Table 2 summarizes the numerical results for mechanical properties;

TABLE 2

Mean values and standard deviations of statistically significant mechanical properties of the anisotropic implants. (n = 4).

|  | E [Mpa] | Flexural Strength [Mpa] | Max Load [N] | Density [gr/ml] | Volume [mm³] |
| --- | --- | --- | --- | --- | --- |
| Amorphous | 3183.15 ± 396.7 | 56.56 ± 6.2 | 6.10 ± 0.73 | 1.46 ± 0.05 | 405.50 ± 49 |
| Parallel | 10572.5 ± 878.2 | 333.1 ± 32.8 | 41.74 ± 6.17 | 1.34 ± 0.066 | 447.67 ± 21 |
| Perpendicular | 483.47 ± 84.4 | 14.22 ± 0.76 | 2.13 ± 0.13 | 1.33 ± 0.021 | 487.26 ± 18.3 |
| Parallel to Amorphous Anisotropocity (%) | 332% | 589% | 684% |  |  |
| Parallel to Perpendicular Anisotropocity (%) | 2189% | 2342% | 1960% |  |  |
| Amorphous to Perpendicular Anisotropocity (%) | 659% | 398% | 286% |  |  |

TABLE 3

Mean values and standard deviations of tensile mechanical properties of the implants (n = 4).

|  | E [MPa] | Tensile Strength [MPa] | Ultimate tensile strain [mm/mm] | Tensile Max Load [N] | Density [gr/ml] | Volume [mm3] |
| --- | --- | --- | --- | --- | --- | --- |
| Tensile Plate (Parallel) | 7700.35 ± 594.7 | 89.65 ± 6.71 | 0.075 ± 0.01 | 752.5 ± 94.8 | 1.47 ± 0.03 | 428.66 ± 48.9 |
| Improvement in mechanical properties as tested in flexural axis as compared with mechanical properties as tested in tensile axis (% of flexural value divided by tensile value) | 137% | 372% |  |  |  |  |

Figure 5:
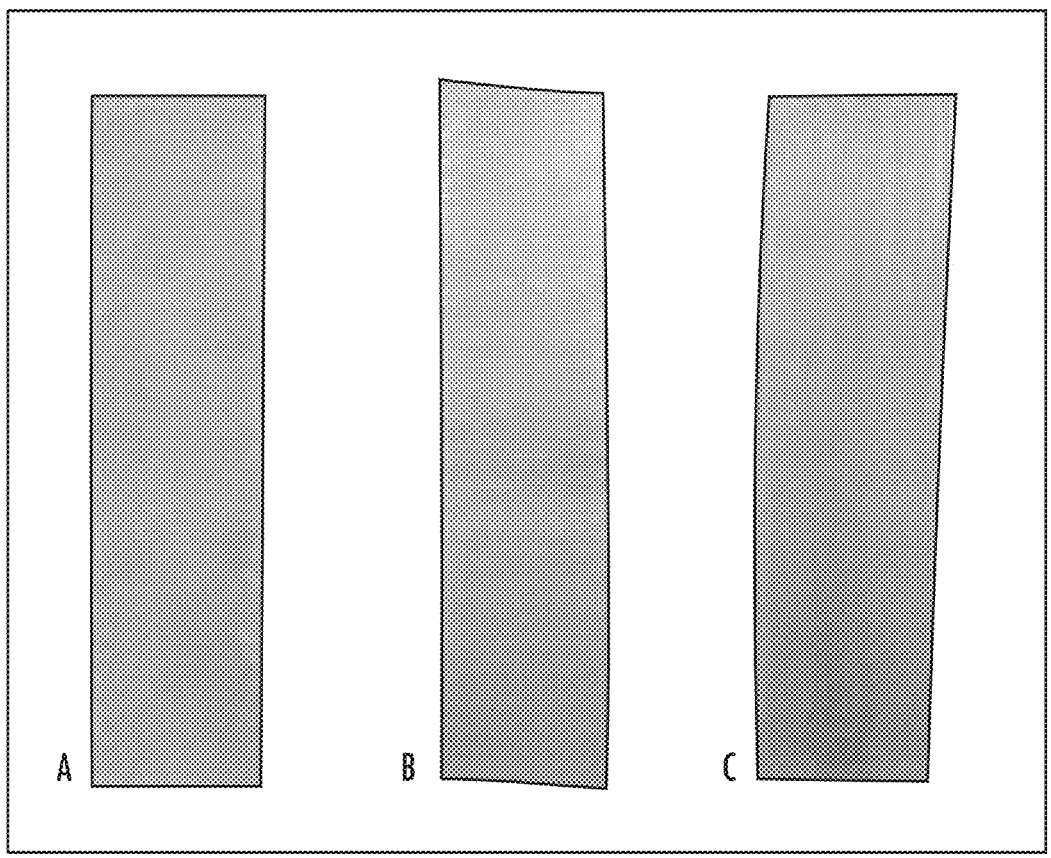
FIGS. 5A-C show representative sample examples.

FIG. 5 shows representative sample examples. FIG. 5A shows an amorphous fiber orientation sample; FIG. 5B shows a sample with majority of layers with fiber orientation perpendicular to implant longitudinal axis. FIG. 5C shows a sample with majority of layers with fiber orientation parallel to implant longitudinal axis. Mechanical properties of sample C were superior to those of samples A and B; however sample A had properties that were superior to sample B, presumably due to the presence of at least some parallel fibers.

Example #3

Example 3 differs from Examples 1 and 2 in that identical material composites were used to produce rectangular plate implants but a different production method was used that resulted in a lower density. This examples shows that such samples with lower density have much inferior mechanical properties as compared with the otherwise similar higher density samples described in examples 1 and 2. Density changes are due to the production method. Without wishing to be limited by a single hypothesis, density depends on how much air or water is incorporated in the implant over the course of production.

Materials and Methods

Rectangular testing samples (dimensions 50.8 mm×12.7 mm×1.1 mm), simulating plates used for small bone fixation, were produced using reinforced composite material. Material composite was as described in Example 1.

Four testing samples were produced, manufactured by a two step process of 1) wrapping two complete layers of composite material around a 40 mm diameter tube using a hot air blower to adhere layers to each other and form a two layer biocomposite tube; 2) cutting biocomposite tube into two sheets and pressing sheets against each other using heated steel blocks. Each layer was 0.18 mm thick. The resulting samples were each comprised of the PLDLA polymer with embedded uni-directionally aligned continuous fibers where orientation of layers relative to longitudinal axis of implant were 8°, −8°, 8°, −8°. This specific alignment was designed to approximate 0° and would be expected to approximate the mechanical properties of the 0° (Parallel) samples described in example 2 if all other parameters were equal.

Implant samples were tested for Flexural strength, Elastic modulus and Maximum load according to ASTM D790-10 with a 500N load cell and a 3 point bending fixture (220Q1125-95, TestResources, MN, USA). Load span was 25.4 mm and cross head speed was set at 0.942 mm/min (Dimensions, weight and density of samples were measured. Statistical comparison between two treatments was performed using a t-test. A confidence level of p=0.05 was used.

Results

Table 4 shows the significance of structural differences between reinforced composites. The alignment with 8 degree fiber offset described herein would be expected to be nearly identical to the parallel fiber alignment described in Example 1, and yet the strength and modulus are drastically lower. Without wishing to be limited by a single hypothesis, it is believed that the much lower density seen in this example (Example 3) was the cause or at least a significantly contributing factor.

TABLE 4

Mean values and standard deviations of the mechanical properties of the anisotropic implant. (n = 4).

|  | E [MPa] | Flexural Strength [MPa] | Max Load [N] | Density [gr/ml] | Volume [mm³] |
|---|---|---|---|---|---|
| 4layers, 8deg | 2052.47 ± 96.55 | 49.24 ± 2 | 18.52 ± 0.43 | 0.935 ± 0.01 | 775.49 ± 17.11 |

Example #4

The below example describes how anisotropic biocomposite implants retain significant mechanical properties (modulus and strength) after exposure to rigorous accelerated degradation conditions.

Materials and Methods

Rectangular testing samples (dimensions 50.8 mm×12.7 mm×1.1 mm), simulating plates used for small bone fixation, were produced using reinforced composite material. Material composite was as described in Example 1.

Eight testing samples were produced, manufactured by compression molding of four or five layers of composite material. Each layer was 0.18 mm thick. In four samples, five layer samples were each comprised of the PLDLA polymer with embedded uni-directionally aligned continuous fibers where orientation of layers relative to longitudinal axis of implant were 0° (parallel to implant longitudinal axis), 45°, 0°, −45°, 0°. In four other samples, four layer samples were each comprised of the PLDLA polymer with embedded uni-directionally aligned continuous fibers where orientation of layers relative to longitudinal axis were 0° (parallel to implant longitudinal axis), 45°, −45°, 0°.

Implant samples were tested for Flexural strength, Elastic modulus and Maximum load according to ASTM D790-10 with a 500N load cell and a 3 point bending fixture (220Q1125-95, TestResources, MN, USA). Load span was 25.4 mm and cross head speed was set at 1.536 mm/min. Implants were tested either at time=0 or after incubation in simulated body fluid (SBF). SBF was comprised of: 142 Na+, 5 K+, 1.5 Mg 2+, 2.5 Ca2+, 147.8 Cl−, 4.2 HCO3−, 1 HPO43−, 0.5 SO4 2− mol/m3. Samples were incubated at either 60 or 50 degrees C. in a shaking incubator (Wis-30 shaking incubator, Witeg, Germany) at 30 rpm for 3-4 days.

Results

Figure 6:
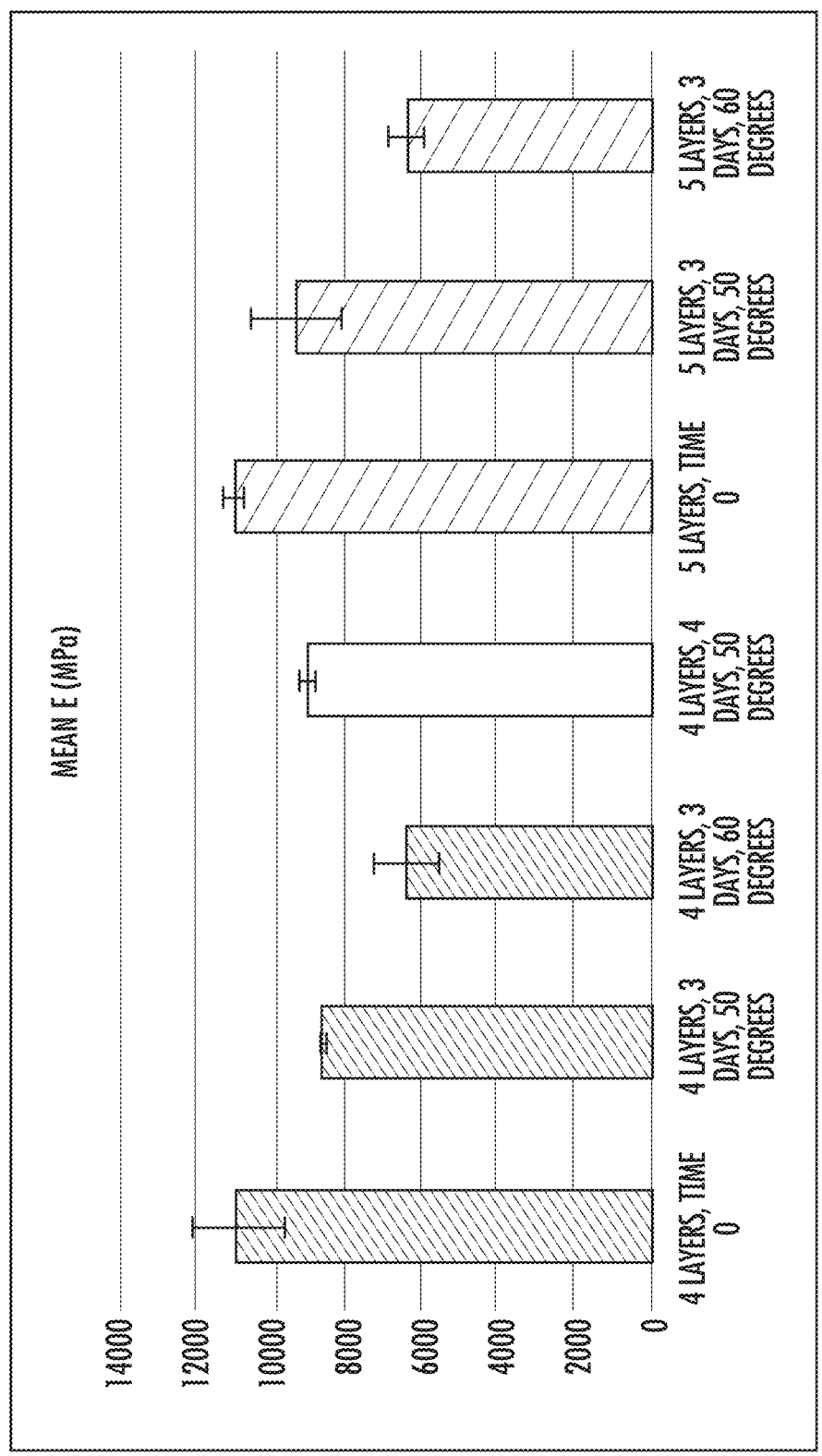
FIG. 6 shows elastic modulus after exposure of exemplary biocomposite samples to forced degradation.
Figure 7:
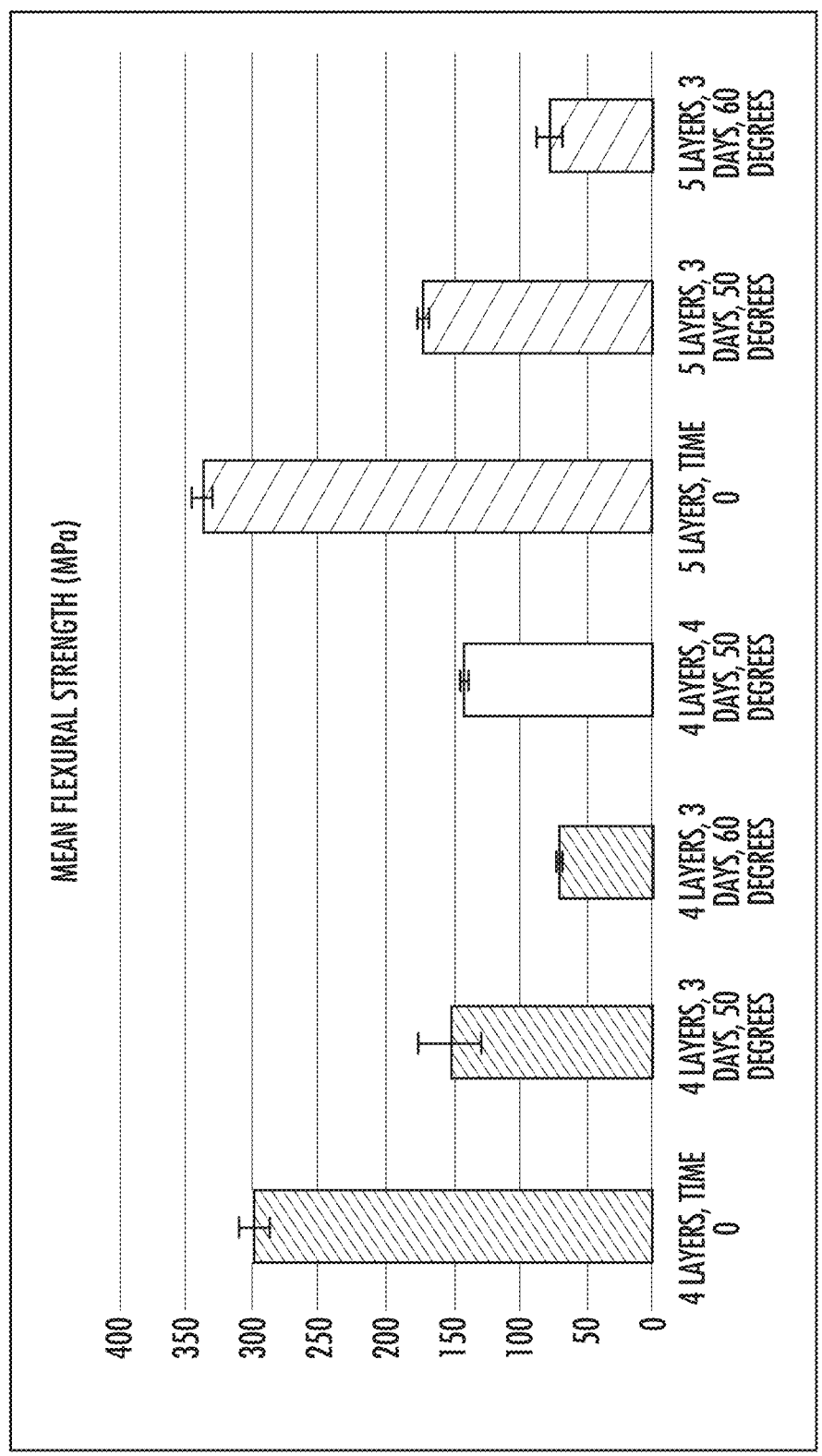
FIG. 7 shows flexural strength after exposure of exemplary biocomposite samples to forced degradation.

FIGS. 6 and 7: After exposure to accelerated degradation conditions of 50° C. for three days, both groups of samples retained >80% of their elastic modulus and >30% of their flexural strength. 50° C. is the highest indicative temperature for incubation conditions for accelerated degradation since the Tg of the biocomposite material is 56 C.) FIG. 6 shows elastic modulus after exposure to forced degradation, while FIG. 7 shows flexural strength after exposure to forced degradation.

Example #5

Below example describes production of hollow pin implants with reinforced biocomposite materials. As with plates, hollow pins with alignment with anisotropic characteristics, result in higher mechanical properties in the desired bending force parameters.

Materials and Methods

Hollow pin implants of dimensions appropriate for small bone fixation (2 mm OD, 1 mm ID, 5 cm) were made of composite material of composition as described in Example 1. Pin implants were manufactured in two steps and two types of pin implants were produced: Parallel alignment and amorphous alignment.

For parallel alignment samples (n=7), plates of 0.5-0.6 mm were produced by compression molding three 0.18 mm thick layers of biocomposite material. Plates were each comprised of the PLDLA polymer with embedded uni-directionally aligned continuous fibers where orientation of layers relative to longitudinal axis of implant were 0° (parallel to implant longitudinal axis), 0°, 0°. Two 5 cm length segments of plate were put into a tube mold such that parallel fiber orientation was also parallel to the longitudinal of the pin. The plate segments were thus molded into tube form to form tubes where orientation of layers relative to longitudinal axis of implant were 0° (parallel to implant longitudinal axis), 0°, 0°.

For amorphous alignment samples (n=3), plates of 0.5-0.6 mm were produced by compression molding three 0.18 mm thick layers of biocomposite material. Plates were each comprised of the PLDLA polymer with embedded continuous fibers that were not uni-directionally aligned but rather the layers were chopped into segments of approximately 3 mm and then molded together into the rectangular plates in bulk. Two 5 cm length segments of plate were put into a tube mold. The plate segments were thus molded into tube form to form tubes with amorphous alignment.

Implant pins samples were tested for Flexural strength, Elastic modulus and Maximum load according to modified ASTM D790-10 with a 500N load cell and a 3 point bending fixture (220Q1125-95, TestResources, MN, USA). Load span was 25.4 mm and cross head speed was set at 2 mm/min.

Flexural modulus was calculated according to:

$$\sigma_{max} = \frac{8F_{max}Ld_0}{\pi(d_0^4 - d_i^4)} \quad (1)$$

Where d0 is the outer diameter of the tube, di is the inner diameter of the tube and L is the support span.

Flexural Elastic modulus was calculated according to:

$$E = \frac{4 mL^3}{3\pi(d_0^4 - d_i^4)} \quad (2)$$

Results

Table 5 shows the numerical summary of the various mechanical parameters for the pins for material aligned in parallel, tested and then calculated as described above. Table 6 shows the corresponding results for amorphous (non-aligned) pins. With the exception of volume and density, pins made from the parallel aligned material had nearly four times as great mechanical properties as pins made from the amorphous material.

TABLE 5

Mean values and standard deviations of mechanical properties for parallel aligned pins as compared with amorphous (non-aligned) pins

| Sample | E [MPa] | Flexural Strength [MPa] | Density [gr/ml] | Max Load [N] | Volume [mm³] |
|---|---|---|---|---|---|
| Parallel Tubes (n = 7) | 8890.74 ± 1209.5 | 158.62 ± 19.3 | 1.47 ± 0.02 | 19.82 ± 3.2 | 121.88 ± 7.06 |
| Amorphous Tubes (n = 3) | 2907.13 ± 730.9 | 40.15 ± 7.8 | 1.35 ± 0.04 | 4.82 ± 0.68 | 138.52 ± 2.96 |
| Parallel to Amorphous Anisotropocity (%) | 306% | 395% | | | |

Figure 8:
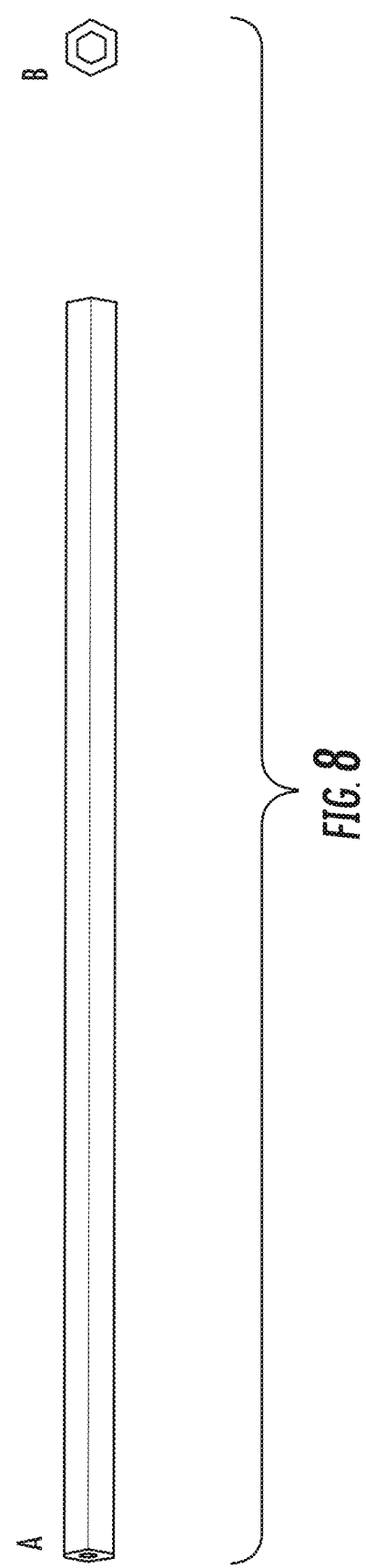
FIGS. 8A and 8B are photographs of a representative hollow pin implant, 5 cm length, 2 mm OD, 1 mm ID.

FIG. 8 is a photograph of a representative hollow pin implant, 5 cm length, 2 mm OD, 1 mm ID. FIG. 8A is a photo of the pin along its length; FIG. 8B is a photo of the cross-section of the pin.

Example #6

Below example describes production of reinforced biocomposite pin implants that are not hollow.

Materials and Methods

Pin implants of dimensions appropriate for small bone fixation (2 mm OD, 5 cm) were made of composite material of composition as described in Example 1. Pin implants were manufactured in two steps. Plates of 0.5-0.6 mm were produced by compression molding three 0.18 mm thick layers of biocomposite material. Plates were each comprised of the PLDLA polymer with embedded uni-directionally aligned continuous fibers where orientation of layers relative to longitudinal axis of implant were 0° (parallel to implant longitudinal axis), 0°, 0°. Four 5 cm length segments of plate were put into a cylinder mold such that parallel fiber orientation was also parallel to the longitudinal of the pin. The plate segments were thus molded into cylinder form to form cylinders where orientation of layers relative to longitudinal axis of implant were 0° (parallel to implant longitudinal axis), 0°, 0°.

Implant pins were tested for Flexural strength, Elastic modulus and Maximum load according to modified ASTM D790-10 with a 500N load cell and a 3 point bending fixture (220Q1125-95, TestResources, MN, USA). Load span was 25.4 mm and cross head speed was set at 2 mm/min.

Flexural modulus was calculated according to:

$$\sigma_{max} = \frac{8F_{max}L}{\pi d_0^3} \quad (1)$$

Where $d_0$ is the outer diameter of the cylinder and L is the support span.

Flexural Elastic modulus was calculated according to:

$$E = \frac{4 \, mL^3}{3\pi d_0^4} \quad (2)$$

Results

TABLE 7

Mean values and standard deviations of mechanical properties (n = 3).

| | E [MPa] | Flexural Strength [MPa] | Density [gr/ml] | Max Load [N] | Volume [mm³] |
|---|---|---|---|---|---|
| Full Cylinders | 9536.53 ± 1348.7 | 202.82 ± 90.7 | 1.403 ± 0.003 | 24.79 ± 10.12 | 169.58 ± 6.6 |

Figure 9:
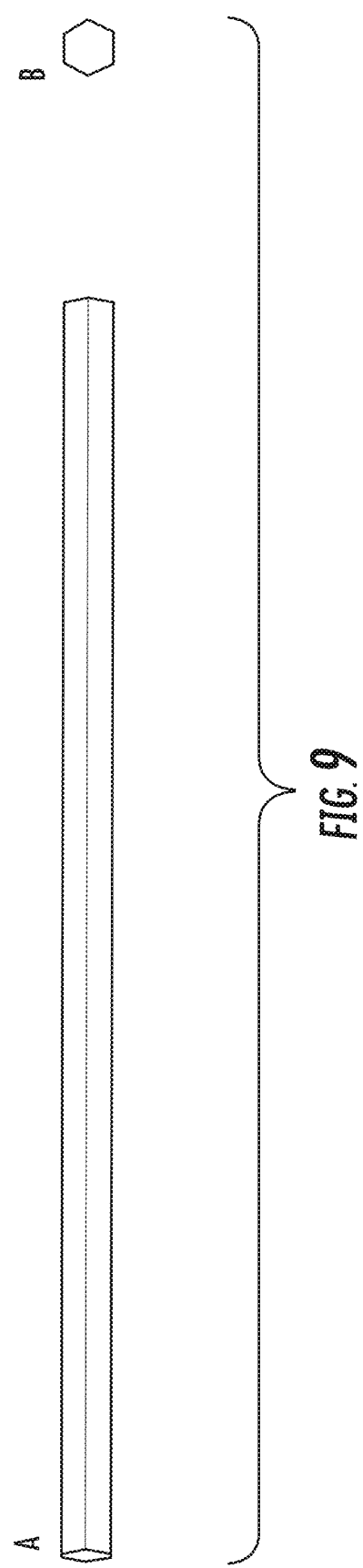
FIGS. 9A and 9B are photographs of a representative pin, 5 cm length, 2 mm OD.

FIG. 9 is a photograph of a representative pin, 5 cm length, 2 mm OD. FIG. 9A is a photo of the pin along its length; FIG. 9B is a photo of the cross-section of the pin.

Example #7

The below example describes how anisotropic biocomposite implants retain a high amount of mechanical properties (modulus and strength) after exposure to degradation conditions.

Materials and Methods

Rectangular testing samples (dimensions 50.8 mm×12.7 mm×0.75 mm), simulating plates used for small bone fixation, were produced using reinforced composite material. Material composite was as described in Example 1.

Samples were produced by compression molding of five layers of composite material. Each layer was 0.18 mm thick. Five layer samples were each comprised of the PLDLA polymer with embedded uni-directionally aligned continuous fibers where orientation of layers relative to longitudinal axis of implant were 0° (parallel to implant longitudinal axis), 45°, 0°, −45°, 0°.

Implant samples were tested for Flexural strength, Elastic modulus and Maximum load according to ASTM D790-10 with a 500N load cell and a 3 point bending fixture (220Q1125-95, TestResources, MN, USA). Load span was 25.4 mm and cross head speed was set at 1.536 mm/min. Implants were tested either at time=0 or after incubation in simulated body fluid (SBF). SBF was comprised of: 142 Na+, 5 K+, 1.5 Mg 2+, 2.5 Ca2+, 147.8 Cl−, 4.2 HCO3−, 1 HPO43−, 0.5 SO4 2− mol/m3. Samples were incubated in SBF at 37 degrees C. in a shaking incubator (Wis-30 shaking incubator, Witeg, Germany) at 30 rpm for five days.

Results

Table 8 shows the mean values and standard deviations of mechanical properties of the implants at t0 (n=2) and after 5 days at 37 C (n=3), demonstrating degradation after this elapsed time.

Figure 10:
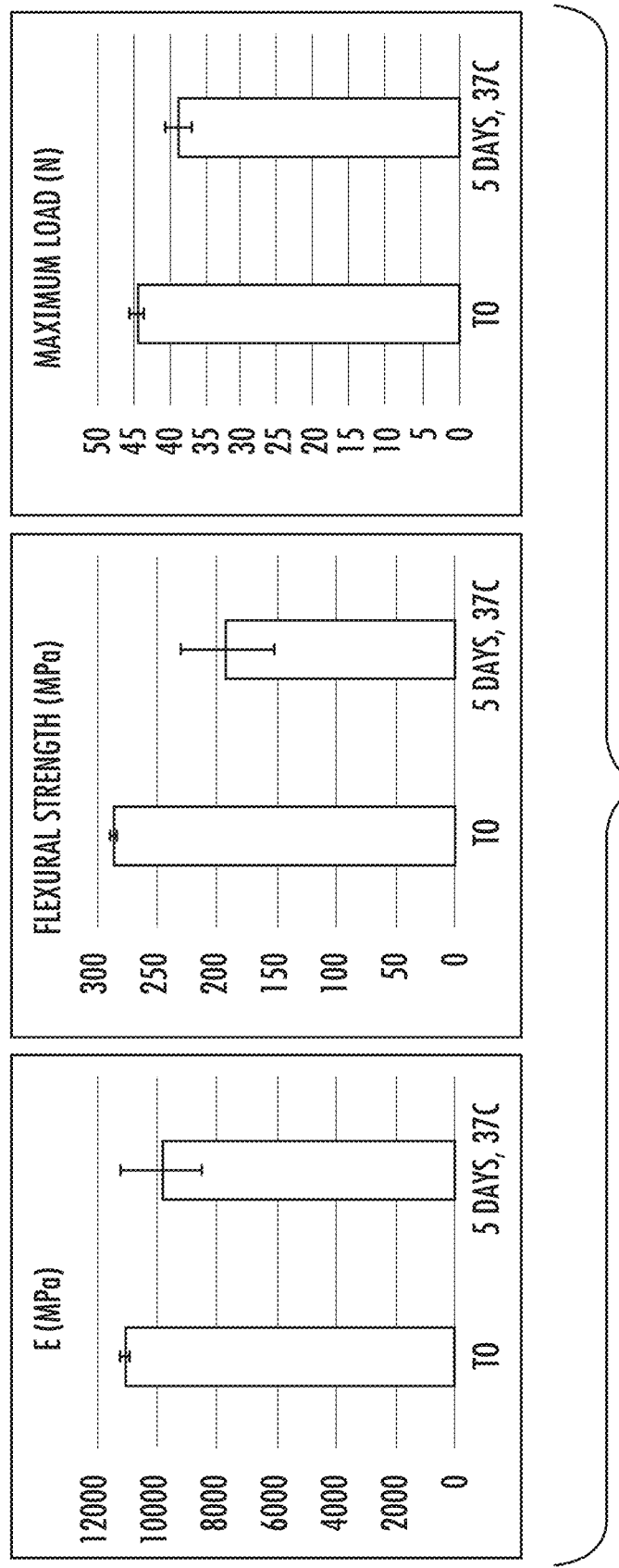
FIG. 10 shows the decrease in mechanical properties due to incubation under conditions that force degradation.

FIG. 10 shows the decrease in mechanical properties due to incubation under conditions that force degradation. These results show that after 5 days of simulated strength degradation, implants retained >60% of flexural strength, >85% of Modulus and Max load.

Additionally, implant swelling was measured following the incubation at 37 C for 5 days, with thickness of implants increasing by 1.9% and overall volume by 2.8%.

Example #8

The below example describes how anisotropic biocomposite implants retain a high amount of mechanical properties (modulus and strength) after exposure to degradation conditions.

Materials and Methods

Rectangular testing samples (dimensions 50.8 mm×12.7 mm×0.75 mm), simulating plates used for small bone fixation, were produced using reinforced composite material. Material composite was as described in Example 1.

Samples were produced by compression molding of five layers of composite material. Each layer was 0.18 mm thick. Five layer samples were each comprised of the PLDLA polymer with embedded uni-directionally aligned continuous fibers where orientation of layers relative to longitudinal axis of implant were 0° (parallel to implant longitudinal axis), 45°, 0°, −45°, 0°.

Implant samples were tested for Flexural strength, Elastic modulus and Maximum load according to ASTM D790-10 with a 500N load cell and a 3 point bending fixture (220Q1125-95, TestResources, MN, USA). Load span was 25.4 mm and cross head speed was set at 1.536 mm/min. Implants were tested either at time=0 or after incubation in simulated body fluid (SBF). SBF was comprised of: 142 Na+, 5 K+, 1.5 Mg 2+, 2.5 Ca2+, 147.8 Cl−, 4.2 HCO3−, 1 HPO43−, 0.5 SO4 2− mol/m3. Samples were incubated in SBF at 37 degrees C. in a shaking incubator (Wis-30 shaking incubator, Witeg, Germany) at 30 rpm for one day.

Results

| | E [MPa] | Flexural Strength [MPa] | Max Load [N] | Density [gr/ml] | Volume [mm³] |
|---|---|---|---|---|---|
| $T_0$ | 10859.44 ± 163.6 | 281.59 ± 2.97 | 43.37 ± 0.91 | 1.47 ± 0.002 | 479.33 ± 12.29 |
| 5 days, 37 C. | 9694.59 ± 1322.5 | 188.24 ± 39.85 | 37.84 ± 1.69 | 1.47 ± 0.03 | 550.05 ± 85.07 |

|  | E [MPa] | Flexural Strength [MPa] | Max Load [N] | Density [gr/ml] | Volume [mm³] |
| --- | --- | --- | --- | --- | --- |
| T0 | 11416.92 ± 403.7 | 289.67 ± 20.9 | 88.45 ± 7.5 | 1.45 ± 0.05 | 668.49 ± 23.5 |
| 24 hrs, 37 C. | 11698.2 ± 502.5 | 260.05 ± 14.2 | 74.04 ± 5.25 | 1.50 ± 0.03 | 638.58 ± 55.2 |

Table 9 shows the mean values and standard deviations of mechanical properties of the implants before and after incubation at 37 C in SBF for 24 hrs (n=4).

After 24 hour incubation, there was no change in elastic modulus, >85% of flexural strength was retained, and >20% of max load.

Example #9

Below example describes production of hollow pin implants with reinforced biocomposite materials. As with plates, hollow pins with alignment with anisotropic characteristics, result in higher mechanical properties in the desired bending force parameters.

Materials and Methods

Hollow pin implants of dimensions appropriate for small bone fixation (2 mm OD, 1 mm ID, 5 cm length) were made of composite material of composition as described in Example 1. Pin implants were manufactured in two steps and two types of pin implants were produced: hollow cylindrical pins and full cylindrical pins.

For hollow pins (n=3), plates of 0.5-0.6 mm were produced by compression molding three 0.18 mm thick layers of biocomposite material. Plates were each comprised of the PLDLA polymer with embedded uni-directionally aligned continuous fibers where orientation of layers relative to longitudinal axis of implant were 0° (parallel to implant longitudinal axis), 0°, 0°. One 5 cm length segment of plate was put into each side of a tube mold (total of two segments) such that parallel fiber orientation was also parallel to the longitudinal of the pin. The plate segments were thus molded into tube form to form tubes where orientation of layers relative to longitudinal axis of implant were 0° (parallel to implant longitudinal axis), 0°, 0°.

For full cylindrical pins (n=3), plates of 0.5-0.6 mm were produced by compression molding three 0.18 mm thick layers of biocomposite material. Plates were each comprised of the PLDLA polymer with embedded uni-directionally aligned continuous fibers where orientation of layers relative to longitudinal axis of implant were 0° (parallel to implant longitudinal axis), 0°, 0°. Four 5 cm length segments of plate were put into a cylindrical mold such that parallel fiber orientation was also parallel to the longitudinal of the pin. The plate segments were thus molded into cylinder form to form cylinders where orientation of layers relative to longitudinal axis of implant were 0° (parallel to implant longitudinal axis), 0°, 0°.

Implant samples were tested for tensile strength, tensile modulus and maximum load according to modified ASTM D3039M with a 5 KN load cell and an appropriate fixture (220Q1125-95, TestResources, MN, USA). Sample span was 30 mm at the beginning of the test and cross head speed was set at 2 mm/min. Dimensions, weight and density of samples were recorded.

Results

Perhaps unsurprisingly, measures of mechanical strength (including elastic module, tensile strength and max load) were all significantly higher for full (non-hollow) pins as compared to hollow pins, as shown in Tables 10 and 11.

TABLE 10

Mean values and standard deviations of mechanical properties of hollow pin implants (n = 3) and full pin implants (n = 3).

|  | E [MPa] | Tensile strength [MPa] | Ultimate tensile strain [mm/mm] | Max Load [N] | Density [gr/ml] | Volume [mm3] |
| --- | --- | --- | --- | --- | --- | --- |
| Hollow Pin Tensile | 8244.3 ± 1379.8 | 78.01 ± 32.6 | 0.026 ± 0.008 | 261.85 ± 113.3 | 1.41 ± 0.06 | 2.548 ± 0.17 |
| Full Pin Tensile | 10724.7 ± 969.7 | 132.9 ± 23.09 | 0.029 ± 0.002 | 431.77 ± 75.9 | 1.43 ± 0.03 | 3.25 ± 0.18 |

Notably, the ratio of modulus as tested in tensile testing between hollow pins and full pins was 0.77 and the ratio of tensile strength was 0.59. For similar pins, as described in examples 5 and 6, the ratio of modulus as tested in flexural testing between hollow pins and full pins was 0.93 and the ratio of flexural strength was 0.78. These results suggest that the same 25% loss in volume between a full and hollow cylindrical geometry results in a different effect on modulus and strength depending on the axis of mechanical testing (tensile or flexural). More strength and modulus are retained for bending resistance (flexural axis) than are retained for elongation resistance (tensile axis) in the hollow geometry.

Example #10

Composite material technology can result in performance unattainable by individual constituents, achieving diverse performance demands that could not be met by one material. A unique combination of strength, stiffness, density and degradation rate is achieved based on the structural composition and orientation of fibers inside the implants.

A mechanical simulations of fiber orientations and structural compositions using the above-described aligned reinforced biocomposite material was performed. The simulation suggested fiber orientations and structural compositions that best fit the bending force load conditions involved in many applications of orthopedic bone fixation. Biomechanical design of implant per clinical application allows for maximizing clinical benefit by reducing implant size and the amount of foreign material being implanted, achieving both required strengths and desired rate of implant absorption.

Figure 11:
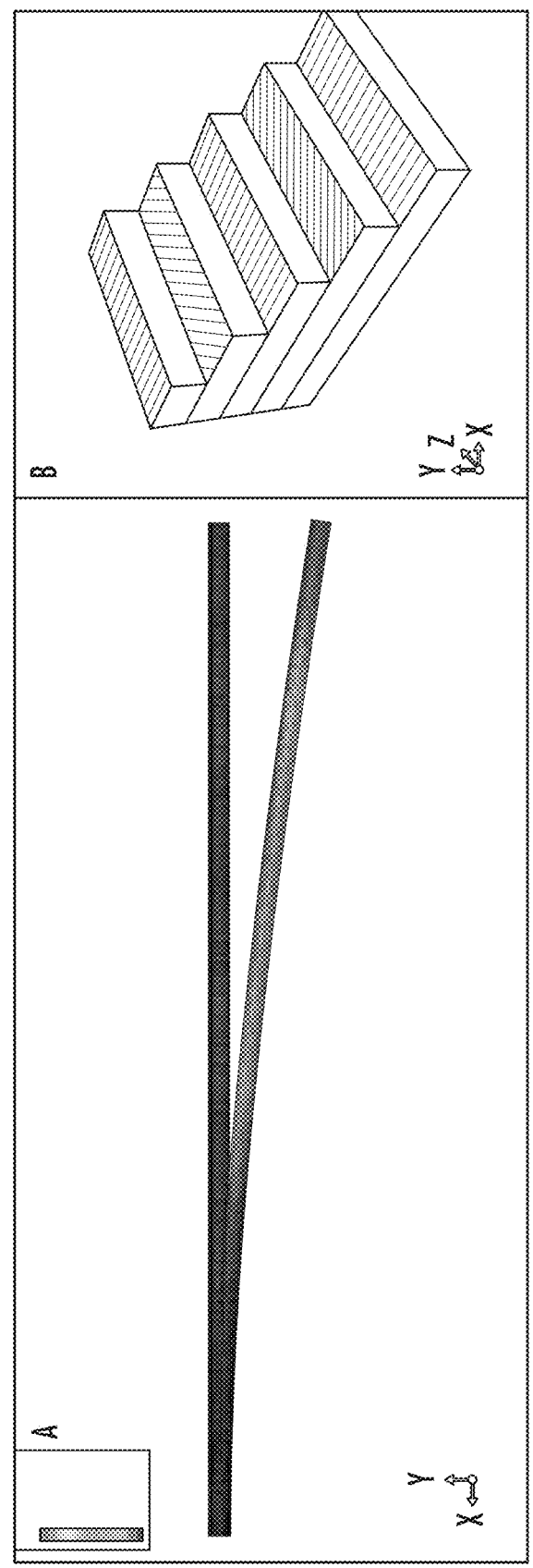
FIGS. 11A and 11B demonstrate a graphical finite elements simulation.

FIG. 11 shows a graphical finite elements simulation. FIG. 11A shows force distribution on a hollow cylinder pin implant with a wall thickness made of 5 layers as demonstrated in FIG. 11B.

Figure 1B:
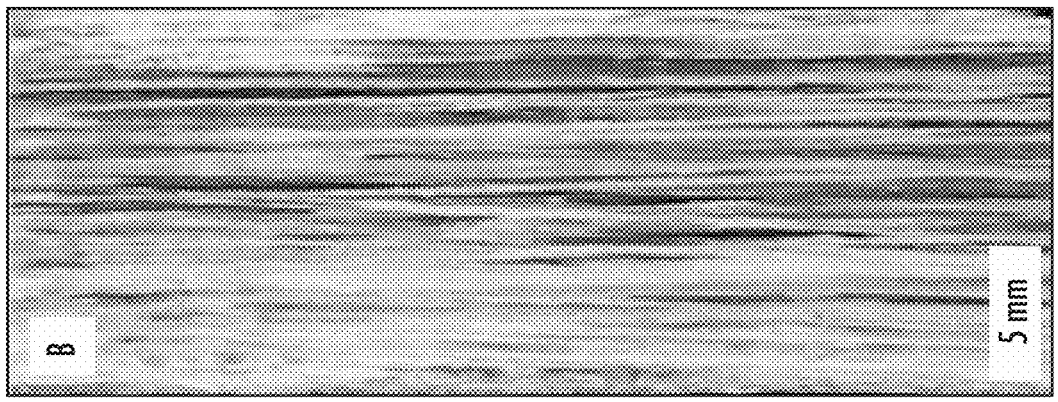
Figure 1A:
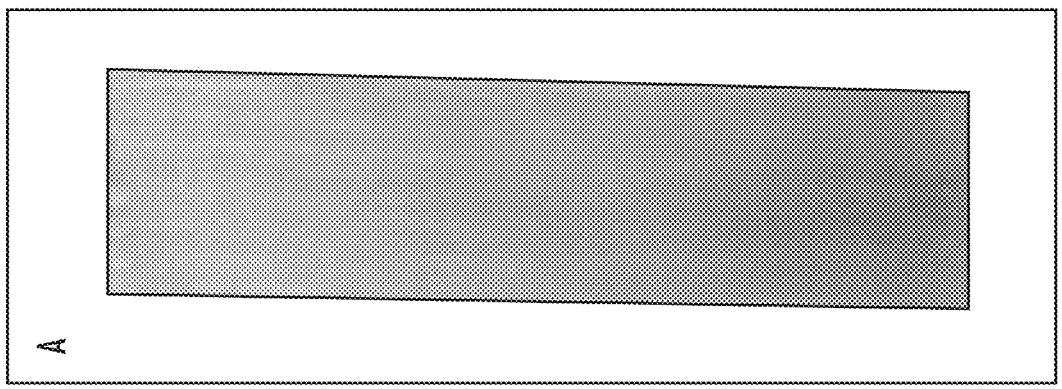

Finite element modeling on a hollow bone fixation pin was performed to evaluate possible layer set ups that can support the expected biomechanical load (FIG. 1). Exact fiber orientation per layer greatly affects the performance of an implant. Table 12 shows how an increase in 10 [N] for the buckling load of an implant in a single direction can be theoretically achieved using different layer structures.

TABLE 12

Finite element simulation results on a 2 mm pin implant for different layer configurations. Orientation presented as: inner (left) to outer (right). Simulation confirms that higher buckling loads can be reached when optimizing layer orientation. In this example optimizing can result in an increase in buckling load from 23 [N] to 32[N]

| Configuration | Bending stiffness [N/mm] | Buckling load [N] |
|---|---|---|
| 0/0/0/45/−45 | 0.554 | 22.7 |
| 45/0/0/0/−45 | 0.589 | 24.0 |
| 0/45/0/−45/0 | 0.591 | 24.2 |
| 45/−45/0/0/0 | 0.626 | 25.7 |
| 20/−20/20/−20/20 | 0.610 | 24.8 |
| 15/−15/15/−15/15 | 0.629 | 29.1 |
| 10/−10/10/−10/10 | 0.788 | 32.5 |

Example 11—Modified Surface Area

This non-limiting, illustrative example describes surface treatment with grit blasting of orthopedic implants comprised of reinforced biocomposite materials. This example demonstrates the changes in the surface properties due to described treatment.

Materials & Methods

An ACL interference screw, outer diameter of 9 mm and 30 mm length, was produced using reinforced composite material. Material composite was comprised of PLDLA 70/30 polymer reinforced with 50% w/w continuous mineral fibers. Mineral fibers composition was approximately Na2O 14%, MgO 5.4%, CaO 9%, $B_2O_3$ 2.3%, $P_2O_5$ 1.5%, and $SiO_2$ 67.8% w/w. Testing samples were manufactured by compression molding of multiple layers of composite material into a screw mold. Each layer was comprised of the PLDLA polymer with embedded uni-directionally aligned continuous fibers. Orientation of layers relative to longitudinal axis of implant were 0° (parallel to implant longitudinal axis), 45°, 0°, −45°, 0°, in a repetitive manner according to number of layers in the implant. Each layer was approximately 0.18 mm thick.

Surface was treated by grit blasting using hydroxyapatite grit (approximately 70 µm average diameter) onto the surface of the implants and rotating the implant for complete coverage.

Scanning electron microscope (FEI Helios 600, Holland) was used to image the implant surface. Images were captured at several magnifications, after Au sputtering, and using EDT detectors.

Results

Figure 12:
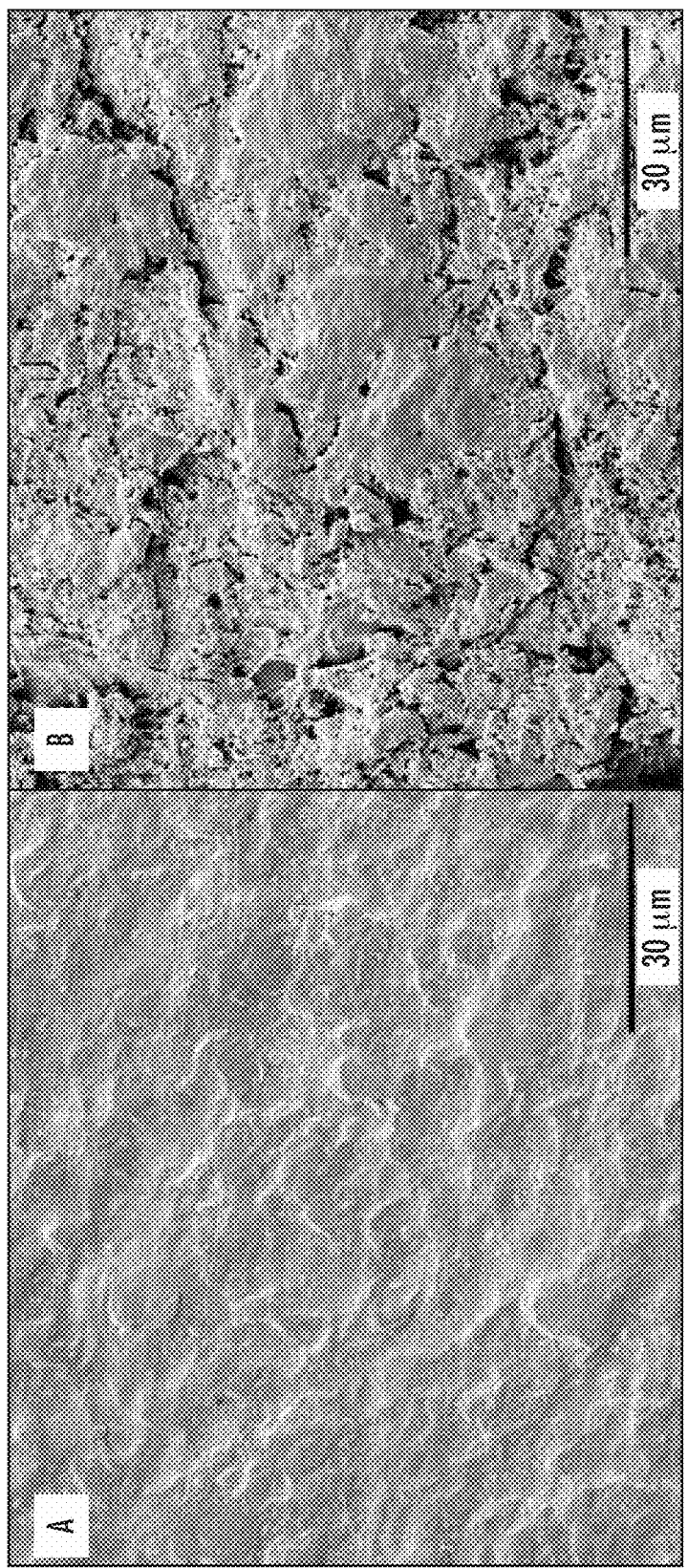
FIG. 12 shows surface texture as imaged by an SEM representing the surface of the implant as it comes out of the mold (A) and after surface treatment (B). Surface roughness is increased, and small nm (nanometer) and micron holes can be seen due to the treatment, which facilitate cell in-growth and degradation.
Figure 13:
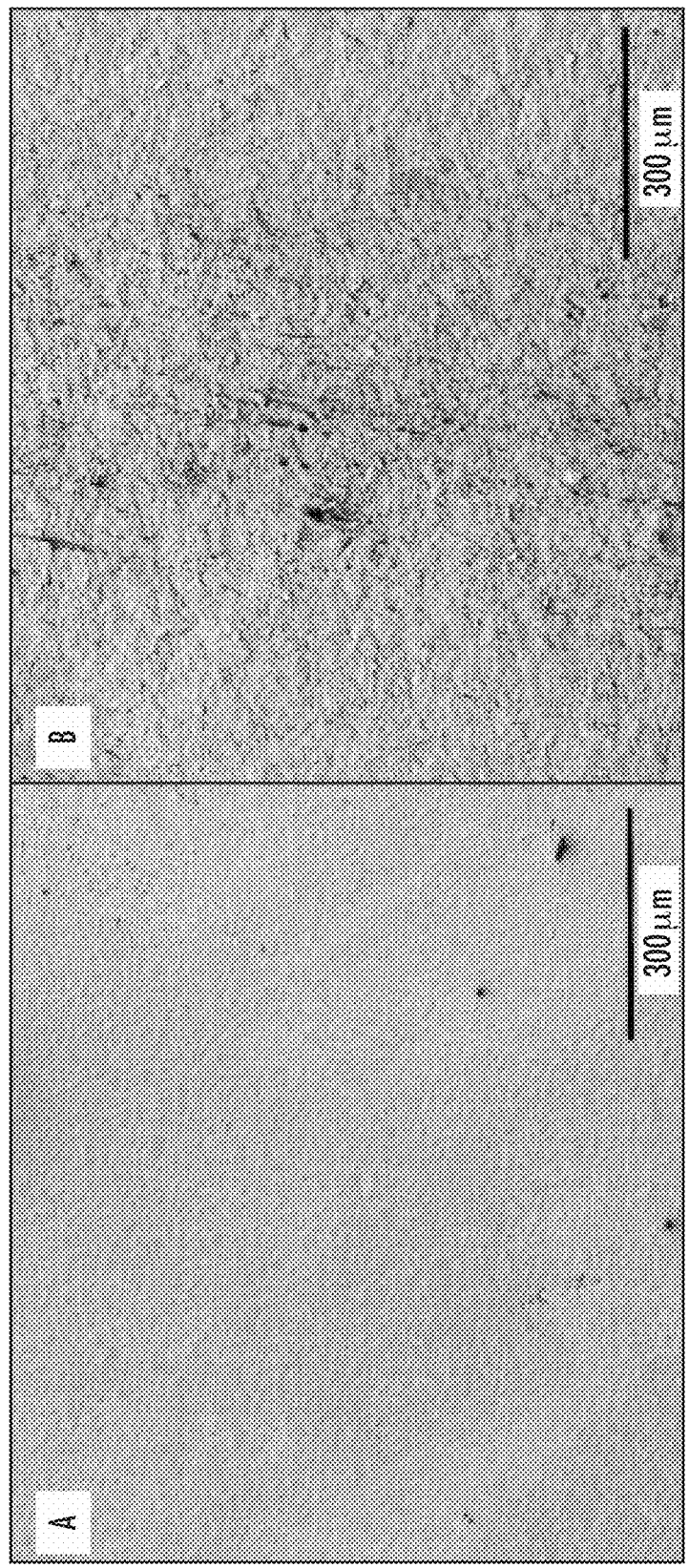
FIG. 13 shows surface texture as imaged by an SEM representing the surface of the implant as it comes out of the mold (A) and after surface treatment (B). Surface roughness is increased. Image was taken at a different magnification.

Surface treatment resulted in an increased in the roughness of the surface as can be seen in FIGS. 12 and 13. This roughness can facilitate improved cell attachment and osseo-integration. Due to the compression molding manufacturing technique the outer layer of the implant is mostly smooth polymer and the mineral component that has the bioactive ingredients is not exposed to the cells. This technique facilitates the integration of the cells into the implant due to the morphological change and increases the degradation of the outer layer of the polymer exposing the bioactive minerals at a faster rate, hence again later increasing the osteo-conductive properties of the implant.

Figure 14:
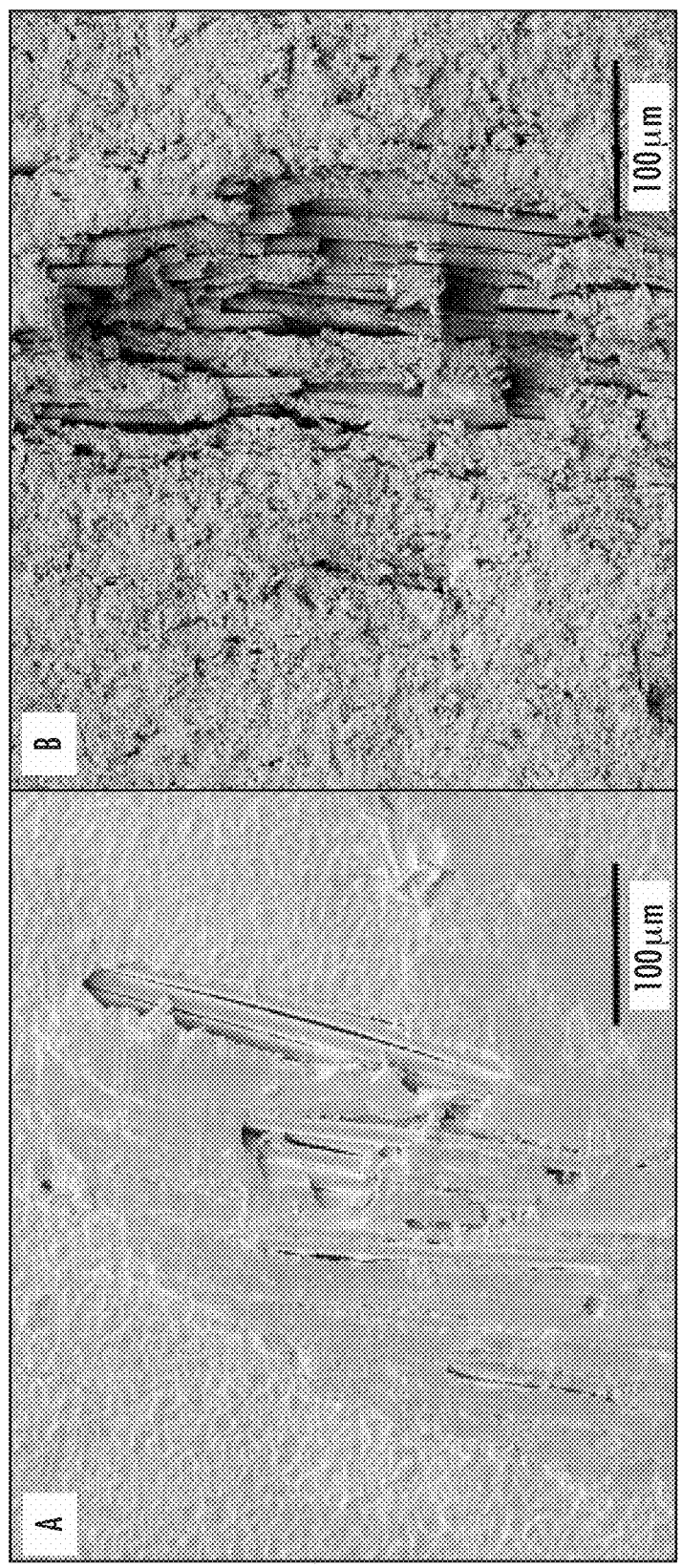
FIG. 14 shows implant mineral fibers partially exposed as imaged by an SEM before treatment (A) and after surface treatment (B). Fiber exposure increased due to the surface treatment.
Figure 15:
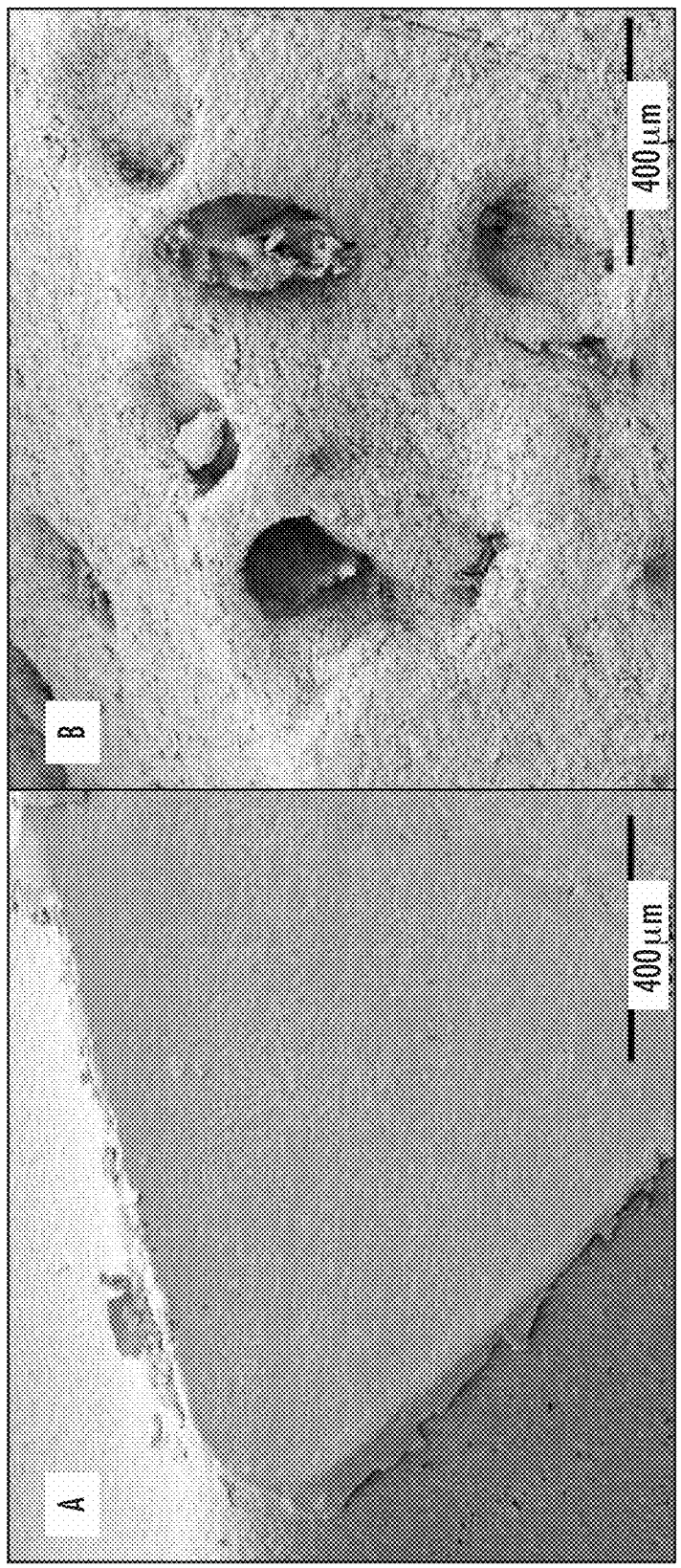
FIG. 15 shows surface texture as imaged by an SEM representing the surface of the implant as it comes out of the mold (A) and after surface treatment (B). Surface roughness is increased, ~200 micron holes can be seen due to the treatment, which facilitate cell in-growth and degradation.

In addition surface treatment seems to increase the exposure of mineral fibers in the specific locations were fibers are close to the implant surface (FIGS. 14 and 15).

Without wishing to be limited by a single hypothesis, it is believed that surface treatment seen in this example can be a significantly contributing factor to an increase in osseointegration.

Example 11—Plates

The below example describes production of thin orthopedic plates with reinforced biocomposite materials. This example demonstrates the different surface properties of medical implant plates comprised of reinforced biocomposite materials due to surface treatments.

Materials & Methods

Plate implants, each with a thickness of 2 mm, width of 12.8 mm and 6 cm length were produced using reinforced composite material. Material composite was comprised of PLDLA 70/30 polymer reinforced with 50% w/w continuous mineral fibers. Mineral fibers composition was approximately $Na_2O$ 14%, MgO 5.4%, CaO 9%, $B_2O_3$ 2.3%, $P_2O_5$ 1.5%, and $SiO_2$ 67.8% w/w. Testing samples were manufactured by compression molding of multiple layers of composite material into a rectangle mold. Each layer was comprised of the PLDLA polymer with embedded uni-directionally aligned continuous fibers. Orientation of layers relative to longitudinal axis of implant were 0° (parallel to implant longitudinal axis), 45°, 0°, −45°, 0°, in a repetitive manner according to number of layers in the implant. Each layer was approximately 0.15 mm thick. Plates were either not treated or treated by blasting using hydroxyapatite grit onto the surface of the implants while rotating the implant for complete coverage under three different blasting conditions.

Scanning electron microscope (FEI Quanta FEG 250, Holland) was used to image the implant surface. Images were captured at several magnifications using EDT& BS detectors. Samples were cut, cross-sections were imaged by the SEM and surface layer thickness was measured based on distance of mineral fibers from implant edge by the SEM program.

SEM-EDS was used for elemental analysis and data was compared between conditions using 15 Kv and a magnification of ×500.

A Focused ion beam setup (FIB) (Helios 600, FEI) was also used to carve a hole and image the cross-section in a treated implant which was coated with Au prior to carving.

Atomic force microscopy (AFM) was used to characterize the surface roughness and surface area increase. AFM measurements were done by using ICON (Bruker, USA) and Bio FastScan (Bruker) Tapping mode, silicon probe TESP (Bruker), spring constant 20-80 N/m, freq. 279-389 kHz.

Results

Figure 16:
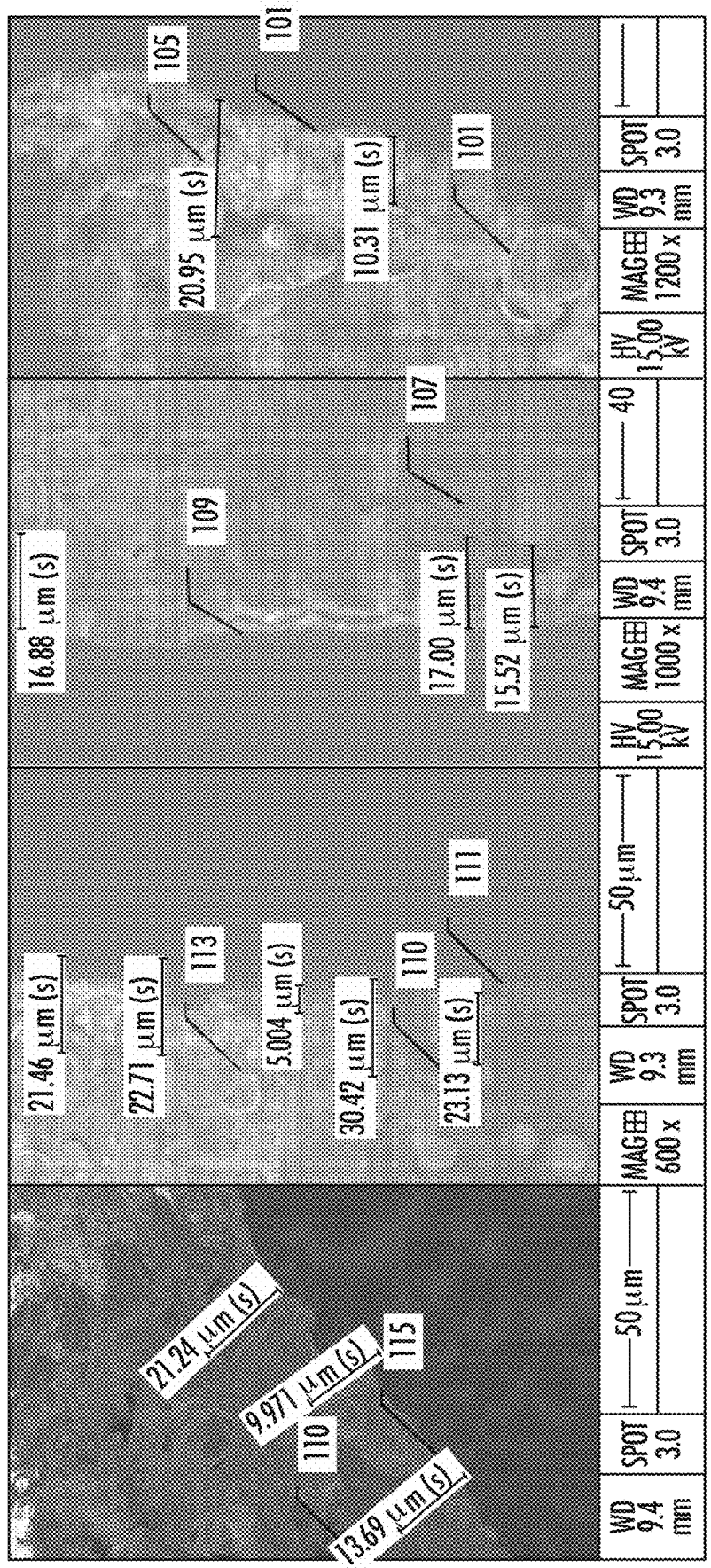
FIG. 16 shows surface cross-section as imaged by a scanning electron microscope (SEM) (FEI Quanta FEG 250, Holland) showing representative measurements of an implant outer surface layer, in this case 17.6±6.8 micron. Reference numbers: 101, 107, 113, 119 represent fibers, 103, 109, 111, 115 represent the polymer edge, 105 represents the measurement from the edge to the closest fiber.
Figure 17:
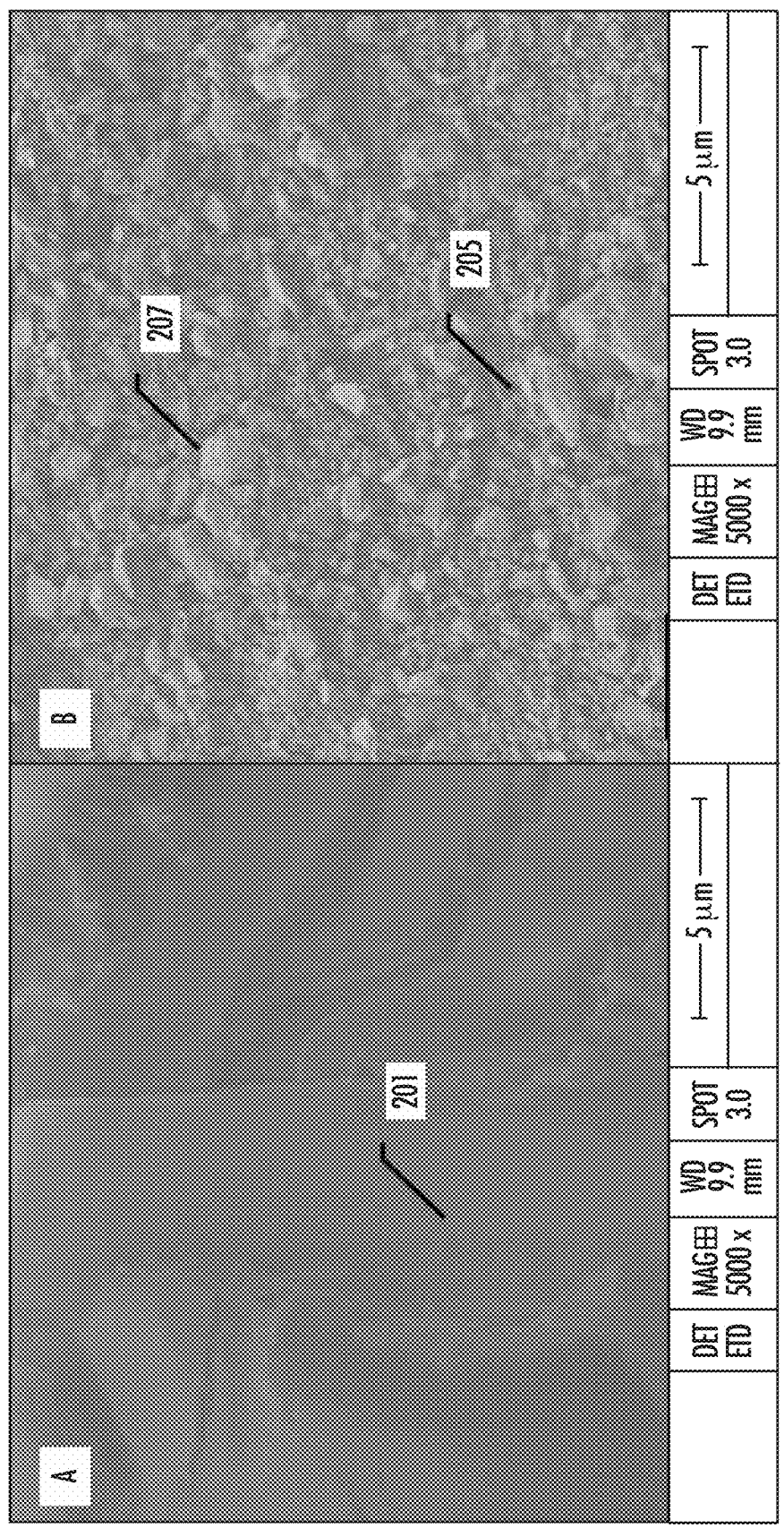
FIGS. 17A and 17B show surface texture as imaged by a scanning electron microscope (SEM) (FEI Quanta FEG 250, Holland) representing the surface of the implant as it comes out of the mold (A) and after surface treatment (B). Surface roughness is increased, small nm and micron holes can be seen due to the treatment, which facilitate cell in-growth and degradation.

Due to the compression molding manufacturing technique the outer layer of the implant is mostly smooth polymer and the mineral component that has the bioactive ingredients which makes up the body of the implant, is not exposed to the cells. In such an implant example the surface layer, defined as the outer mostly polymer layer, was measured to be 17.6±6.8 micron (FIG. 16). Surface treatment resulted in an increased in the roughness of the surface as can be seen in FIGS. 17A and 17B. In 201 the surface is relatively smooth in compare to 205 and 207. This roughness can facilitate improved cell attachment and osseo-integration. This blasting technique facilitates the integration of the cells into the implant due to the morphological change and increases the degradation of the outer layer of the polymer exposing the bioactive minerals at a faster rate, hence again later increasing the osteo-conductive properties of the implant. In addition, surface treatment increases surface area by up to 64% (Table 13). Roughness and roughness max was increased from 35.8 nm to 433 nm and from 0.357 micron to 5.2 micron due to treatments, respectively. Table 13 summarizes the increased roughness parameters both Ra, Ra max and surface areas for three treatments.

body section of the implant. The roughness on the surface in 307 was zoomed in to reveal features around 1 micron in diameter (313).

Elemental composition differences were noted between the implant body, implant inner surface layer and outer surface layer (Table 14). Specifically a decrease in mineral content can be seen between the inner surface and the body of the implant. A decrease in Si content can be seen in the outer surface vs the body of the implant. In this case the phosphate and calcium concentrations are significantly higher in the outer surface layer and not detected in both the inner surface layer as well as the implant body. In this case the body implant composition was also characterized as having more sodium than the surface area, both inner and outer.

TABLE 14

| Element | A Implant body (Mid Implant) | | B Inner Surface Layer (No treatment) | | C Outer Layer (SF1) | |
|---|---|---|---|---|---|---|
| | Wt % Avg | At % Avg | Wt % Avg | At % Avg | Wt % Avg | At % Avg |
| C | 43.71 ± 4.62 | 54.33 ± 4.34 | 51.48 ± 2.5 | 59.57 ± 2.1 | 19.74 ± 1.55 | 31.27 ± 1.375 |
| O | 37.998 ± 1.4 | 35.57 ± 2.24 | 43.48 ± 0.77 | 37.79 ± 1.14 | 39.91 ± 2.41 | 47.49 ± 1.21 |
| Na | 4.54 ± 0.77 | 2.97 ± 0.58 | 1.39 ± 0.42 | 0.84 ± 0.27 | 0.257 ± 0.44 | 0.21 ± 0.36 |
| Mg | 0.98 ± 0.16 | 0.6 ± 0.12 | 0.157 ± 0.27 | 0.09 ± 0.16 | 0.42 ± 0.1 | 0.32 ± 0.06 |
| Si | 10.84 ± 2.26 | 5.8 ± 1.37 | 3.32 ± 1.07 | 1.65 ± 0.55 | \ | \ |
| P | \ | \ | \ | \ | 12.77 ± 0.81 | 7.87 ± 0.76 |
| Ca | 1.92 ± 0.24 | 0.72 ± 0.1 | 0.17 ± 0.3 | 0.06 ± 0.1 | 26.91 ± 3.62 | 12.84 ± 2.16 |

| Element | D Outer Layer (SF2) | | E Outer Layer (SF3) | |
|---|---|---|---|---|
| | Wt % Avg | At % Avg | Wt % Avg | At % Avg |
| C | 30.19 ± 2.15 | 42.66 ± 2.12 | 25.78 ± 3.9 | 38.1 ± 4.17 |
| O | 41.4 ± 1.75 | 43.95 ± 1.59 | 39.88 ± 1.56 | 44.38 ± 0.42 |
| Na | 0.14 ± 0.25 | 0.11 ± 0.2 | 0.7 ± 0.9 | 0.56 ± 0.725 |
| Mg | 0.32 ± 0.05 | 0.22 ± 0.03 | 0.46 ± 0.14 | 0.34 ± 0.11 |
| Si | 0.28 ± 0.48 | 0.17 ± 0.3 | 2.55 ± 3.715 | 1.67 ± 2.45 |
| P | 9.1 ± 0.75 | 5 ± 0.52 | 9.58 ± 0.76 | 5.5 ± 0.52 |
| Ca | 18.57 ± 1.82 | 7.89 ± 0.95 | 20.79 ± 1.5 | 9.26 ± 0.985 |

TABLE 13

| Condition | Roughness (Ra) [nm] | Roughness Rmax [um] | Surface area Difference |
|---|---|---|---|
| No treatment (A) | 35.8 | 0.357 | 0.13% |
| Treatment 1 (B) | 433 | 2.287 | 17% |
| Treatment 2 (C) | 326 | 3.5 | 64.2% |
| Treatment 3 (D) | 388 | 5.2 | 58.3% |

Specifically, Table 13 shows surface roughness measurements done with an Atomic force microscope (AFM) (ICON (Bruker, USA) and Bio FastScan (Bruker, USA) representing (A) the surface of the implant as it comes out of the mold (B, C, D) the surface after blasting with three different conditions. AFM measurements were done by using ICON (Bruker, USA) and Bio FastScan (Bruker), tapping mode, silicon probe TESP (Bruker), spring constant 20-80 N/m, freq. 279-389 kHz.

Figure 18:
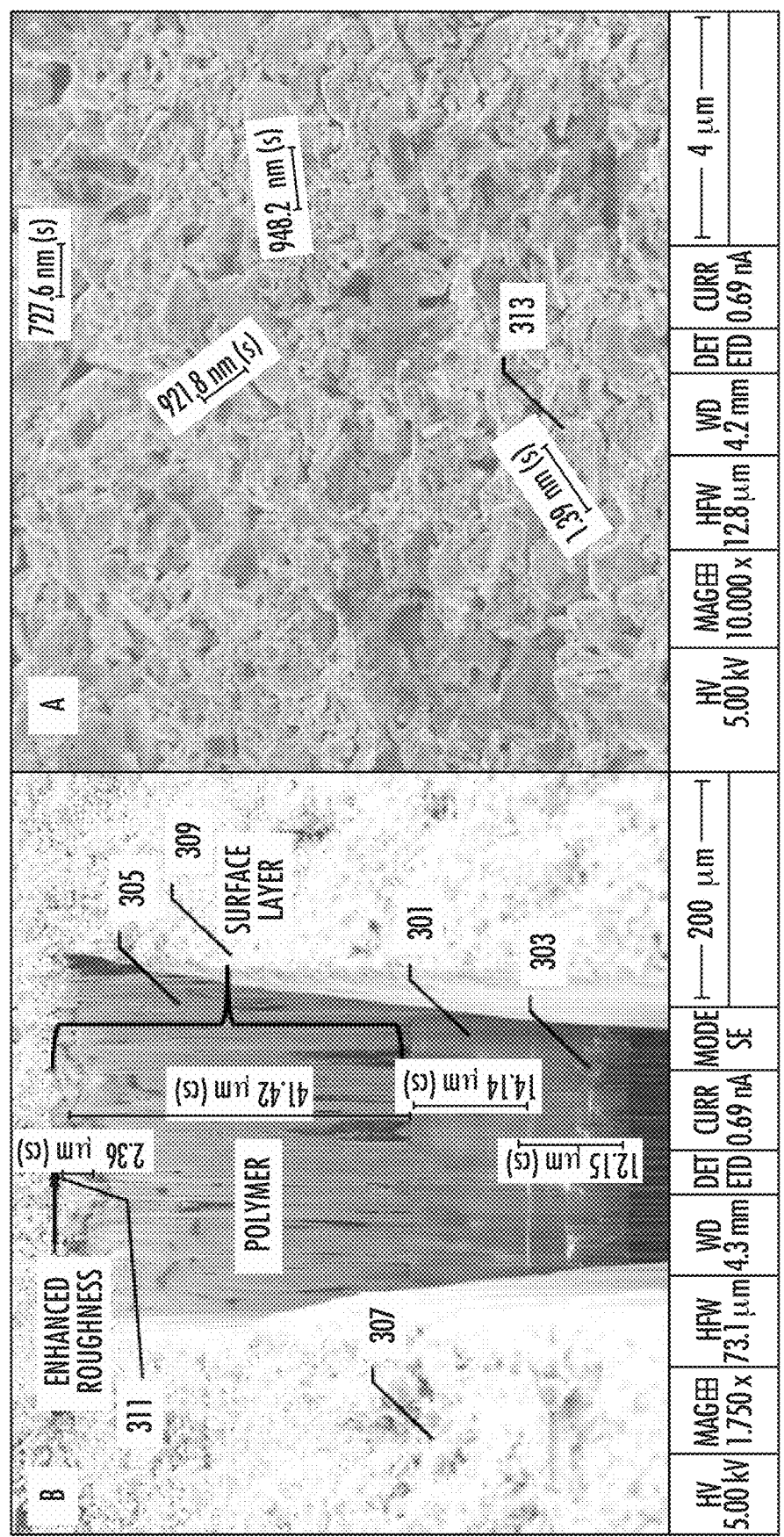
FIGS. 18A and 18B show images by a Focused ion beam setup (FIB) (Helios 600, FEI) representing (A) the surface of the implant after treatment which creates ~1 micron features and (B) a cross-section cut made by the FIB showing representative dimensions of a 45 micron surface layer which has a different composition than the inner material. Surface includes in this case a combination of a ~2.5 micron outer thick layer were the roughness is increased, small nm and micron holes can be seen due to the treatment, which facilitate initial cell attachment and ~40 micron layer of polymer. The cross section of the two mineral fibers can also be seen in the image.

A hole was carved into an implant using a FIB setup exposing an inner crossection of more than 60 micron deep (FIGS. 18A and 18B). In this case an outer surface layer was observed as approximately 2.5 micron (311) and the inner surface layer as an additional 40 micron (305). The crossection of two overlapping mineral fibers can be seen in this image as well (301, 303). They represent the edge of the body section of the implant.

Table 14 shows that energy-dispersive X-ray spectroscopy (EDS) measurements of elemental composition representing (A) the center of the implant cross-section, (B) the surface of the implant as it comes out of the mold (C, D, E) the surface after three different treatments which increases roughness and creates small nm and micron holes, which facilitate cell in-growth and degradation.

Example 12—Small Diameter Pins

This Example describes production of small diameter orthopedic pins with reinforced biocomposite materials. This example demonstrates how medical implant pins comprised of reinforced biocomposite materials can have surface areas of several compositions.

Materials & Methods

Pin implants, each of outer diameter 2 mm and 7 cm length, were produced using reinforced composite material. Material composite was comprised of PLDLA 70/30 polymer reinforced with 50% w/w. Mineral fibers composition was approximately $Na_2O$ 14%, MgO 5.4%, CaO 9%, $B_2O_3$ 2.3%, $P_2O_5$ 1.5%, and $SiO_2$ 67.8% w/w. Testing samples were manufactured by compression molding of multiple layers of composite material into a multi-tubular mold. Each mold was designed to create simultaneously 14 implants. Each layer was comprised of the PLDLA polymer with embedded uni-directionally aligned continuous fibers. Orientation of layers relative to longitudinal axis of implant were 0° (parallel to implant longitudinal axis), 45°, 0°, −45°, 0°, in a repetitive manner according to number of layers in the implant. Each layer was approximately 0.15 mm thick. After extraction of the pins from the molds Computer Numerical Control (CNC) machining was used to separate the 14 pins and to create an angled tip.

Scanning electron microscope (SEM) (FEI Quanta FEG 250, Holland) images were captured for surface and for cross-sections of implant samples at several magnifications and using either EDT or BSE detectors. ImageJ™ (NIH Image Processing Software) was used to measure the surface percentage differences based on the circumference.

SEM-EDS was used for elemental analysis and data was compared between conditions using 15 Kv and a magnification of ×500.

Results

Figure 19:
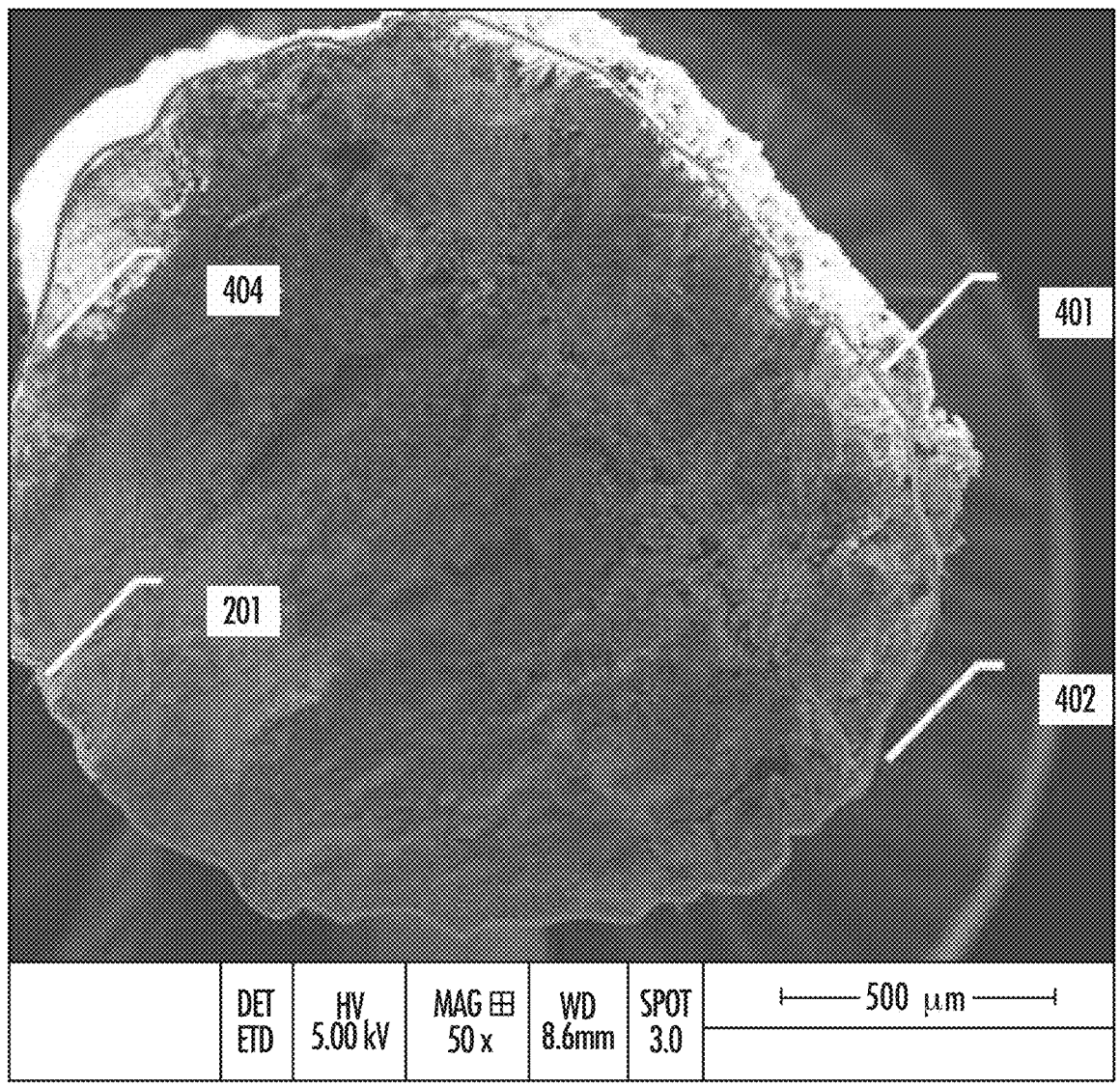
FIG. 19 shows an implant cross-section imaged by a scanning electron microscope (SEM) (FEI Quanta FEG 250, Holland) representing an implant where less than 60% of the circumference, which represents the less than 60% of the surface area is different in composition than the inner composition of the implant.

Computer Numerical Control (CNC) machining which separated the pins was used to expose the inner content of the biocomposite, creating a pin implant which has a surface layer of less than 60% with a different composition than the inner body (FIG. 19). Table 15 provides a key to the drawing.

TABLE 15

| Label | L (μm) | % of Circumference |
|---|---|---|
| Surface layer with different composition (Red, 404 + 402) | 4073.5 | 59% |
| Exposed inner content on surface (Green, 403 + 401) | 2863.9 | 41% |

Figure 20:
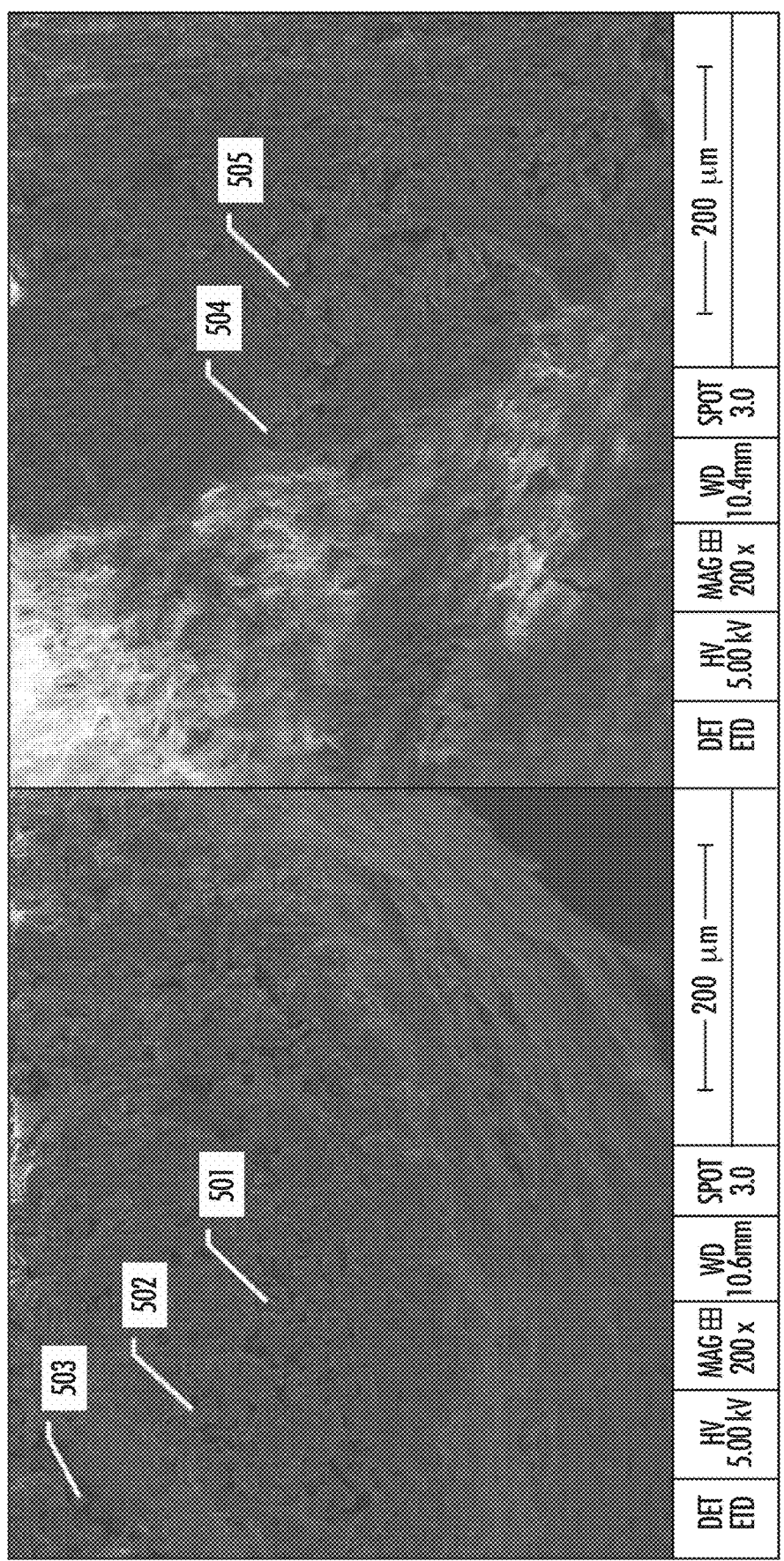
FIG. 20 shows surface texture as imaged by a scanning electron microscope (SEM) (FEI Quanta FEG 250, Holland) representing the surface of the implant after CNC machining treatment which partially exposes fiber bundles (white arrows). Exposed fibers can be seen due to the treatment, which facilitate cell in-growth and degradation.
Figure 21:
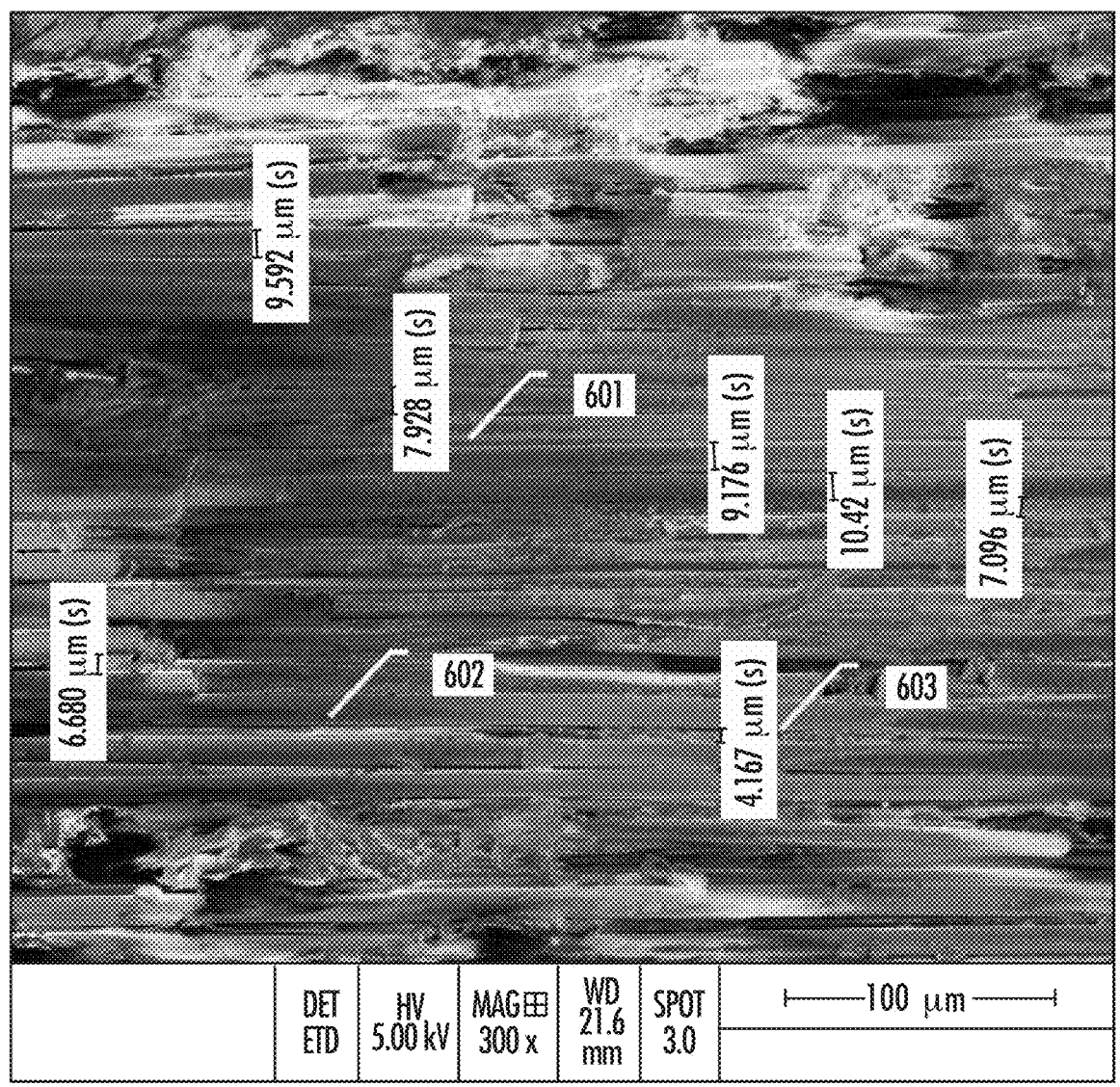
FIG. 21 shows an image demonstrating continuous fiber body composition.
Figure 22:
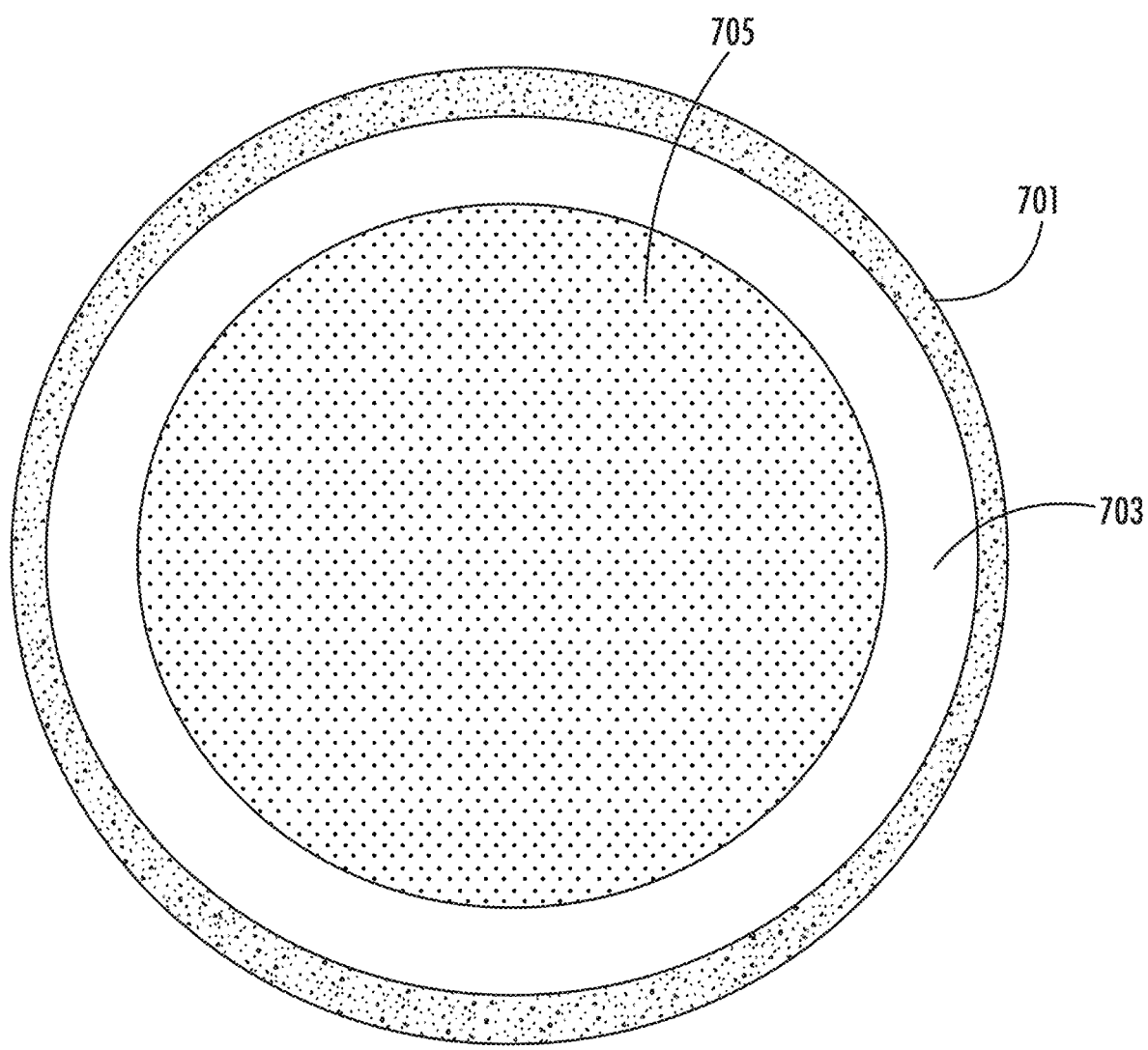
FIG. 22 shows schematics of a representative implant cross-section. Schematics are not in scale, but include the implant body comprised of one composition, 705, the surface layer which in this case includes both an inner surface layer 703 and an outer surface layer 701, each with a different composition.

CNC machining treatment to the tip (FIG. 20) resulted in partially exposed fiber bundles (501-507). Exposed fibers can be seen due to the treatment, these facilitate cell in-growth. Continuous fiber body composition can be seen in FIG. 21, which include representative measurements of fiber diameters, as seen in 601-602 and distances between fibers (603). This body composition is an example of ~1:1 mineral to polymer w/w ratio. FIG. 22 shows schematics of a representative pin implant cross-section when created in a single-tubular mold (unlike the above multi-tubular mold) followed by the blasting treatment described in previous example. Schematics are not in scale, but include the implant body comprised of one composition, 705, the surface layer which in this case includes both an inner surface layer 703 and an outer surface layer 701, each with a different composition. This method results in an outer surface layer which is entirely of a different composition than the inner body.

It will be appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination. Various sub-embodiments may be combined in various combinations, even if not explicitly described herein. It will also be appreciated by persons skilled in the art that the present invention is not limited by what has been particularly shown and described hereinabove.

All references cited or described herein are hereby incorporated by reference as if set forth herein to the extent necessary to support the description of the present invention and/or of the appended claims.

Although the invention has been described in conjunction with specific embodiments thereof, it is evident that many alternatives, modifications and variations will be apparent to those skilled in the art. Accordingly, it is intended to additionally embrace all such alternatives, modifications and variations that fall within the spirit and broad scope of the appended claims.

What is claimed is:

1. An implant with a body composition of mineral and polymer with a surface comprising a different composition than the implant body, wherein 10-70% w/w of the body composition comprises mineral material, wherein said material comprises 1-15% w/w calcium, wherein the body comprises an interspersed composition of mineral and polymer, and a surface layer, wherein said surface layer comprises a surface composition of at least 10% of the surface that is of a different composition than the body composition and comprises less than 4% w/w silica; wherein the body comprises more than 8% w/w silica; wherein the calcium content of the surface is 50% w/w less than the calcium content of the body composition; and wherein the mineral to polymer weight ratio in the surface composition is less than 50% of mineral to polymer weight ratio than the body composition.

2. The implant of claim 1, wherein 30-55% w/w of the body composition comprises mineral material.

3. The implant of claim 2, wherein 45-55% w/w of the body composition comprises mineral material.

4. The implant of claim 1, wherein said polymer comprises poly (L-co-D, L lactic acid) (PLDLA).

5. The implant of claim 1, wherein said mineral material of said body composition comprises ranges of the following compounds, all mol %:
$Na_2O$: 11.0-19.0 mol %;
CaO: 9.0-14.0 mol %;
MgO: 1.5-8.0 mol %;
$B_2O_3$: 0.5-3.0 mol %;
$Al_2O_3$: 0-0.8 mol %;
$P_2O_3$: 0.1-0.8 mol %; and
$SiO_2$: 67-73 mol %.

6. The implant of claim 1, wherein said mineral material of said body composition comprises ranges of the following compounds, all mol %:
$Na_2O$: 12.0-13.0 mol %;
CaO: 9.0-10.0 mol %;
MgO: 7.0-8.0 mol %;
$B_2O_3$: 1.4-2.0 mol %;
$P_2O_3$: 0.5-0.8 mol %; and $SiO_2$: 68-70 mol %.

7. The implant of claim 1, wherein said mineral material of said body composition comprises ranges of the following compounds, all mol %:
$Na_2O$: 11.0-19.0 mol %;
CaO: 8.0-14.0 mol %;
MgO: 2-8.0 mol %;
$B_2O_3$: 1-3.0 mol %;
$Al_2O_3$: 0-0.5 mol %;
$P_2O_3$: 1-2 mol %; and $SiO_2$: 66-70 mol %.

8. The implant of claim 1, wherein more than 30% of the surface is of a different composition than the body.

9. The implant of claim 8, wherein more than 50% of the surface is of a different composition than the body.

10. The implant of claim 1, wherein a portion of the surface layer is treated to partially expose a body composition, and wherein the treated portion of the surface layer has a roughness increase by more than five times the untreated surface.

11. The implant of claim 10, wherein the treated portion of the surface layer has a roughness increase by more than ten times the untreated surface.

12. The implant of claim 11, wherein the treated surface area increases the surface area by more than 15%.

13. The implant of claim 12, wherein the treated surface area increases the surface area by more than 50%.

14. The implant of claim 10 wherein the surface maximum roughness is more than 2 microns.

15. The implant of claim 14, wherein the surface maximum roughness is more than 3 microns.

16. The implant of claim 1, comprising an absorbable structural material, comprising a resorbable, reinforcement filler, characterized in that strength and stiffness properties are anisotropic of at least 10%, at least 20% at least 30%, 40%, 50%, 60%, 70'%, 80%, 90% or 100%, or any number in between, wherein said implant is reduced in volume as compared to an equivalent implant that is not constructed of said absorbable structural material.

17. The implant of claim 16, comprising a load bearing absorbable bone implant, wherein said load is at least 200 MPa, above 300 MPa, above 400 MPa; and wherein said implant has a similar stiffness to cortical bone.

18. The implant of claim 1, wherein the biodegradable composite has a maximum flexural modulus in the range of 6 GPa to 30 GPa and flexural strength in the range of 100 MPa to 1000 MPa.

19. The implant of claim 1, wherein said biodegradable composite comprises a biodegradable polymer; wherein said biodegradable polymer comprises a homopolymer or copolymer; wherein said copolymer comprises a random copolymer, block copolymer or graft copolymer, wherein said polymer comprises a linear polymer, a branched polymer, or a dendrimer, of natural or synthetic origin; wherein said polymer comprises lactide, glycolide, caprolactone, valerolactone, carbonates, dioxanones, δ-valerolactone, 1,dioxepanones, ethylene glycol, ethylene oxide, esteramides, γ-hydroxyvalerate, β-hydroxypropionate, alpha-hydroxy acid, hydroxybuterates, poly (ortho esters), hydroxy alkanoates, tyrosine carbonates, polyimide carbonates, polyimino carbonates, (polyurethanes, polyanhydrides, polymer drugs, sugars; starch, cellulose and cellulose derivatives, polysaccharides, collagen, chitosan, fibrin, hyaluronic acid, polypeptides, proteins, poly (amino acids), polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, terpolymers of PLA, polydepsipeptides; unsymmetrically—3,6-substituted poly-1,4-dioxane-2,5-diones; polyhydroxyalkanoates; PHB/b-hydroxyvalerate copolymers (PHB/PHV); poly-b-hydroxypropionate (PHPA); poly-p-dioxanone (PDS); poly-d-valerolactone-poly-ε-capralactone, poly(ε-caprolactone-DL-lactide) copolymers; methylmethacrylate-N-vinyl pyrrolidone copolymers; polyesteramides; polyesters of oxalic acid; polydihydropyrans; polyalkyl-2-cyanoacrylates; polyurethanes (PU); polyvinylalcohol (PVA); polypeptides; poly-b-malic acid (PMLA): poly-b-alkanbic acids; polycarbonates; polyorthoesters; polyphosphates; poly(ester anhydrides); and mixtures thereof; and derivatives, copolymers and mixtures thereof.

20. The implant of claim 1, wherein the polymer is in a form of a polymer matrix; wherein said polymer matrix comprises a polymer selected from the group consisting of PLLA (poly-L-lactide), PDLLA (poly-DL-lactide) PLDLA (poly (L-co-D,L lactic acid), PGA, (poly-glycolic acid) PLGA (poly-lactide-glycolic acid) PCL (Polycaprolactone) PLLA PCL and a combination thereof.

21. The implant of claim 20, wherein if PLLA is used, the matrix comprises at least 30% w/w, 50% w/w, or at least 70% w/w PLLA.

22. The implant of claim 20, wherein if PDLA is the matrix comprises at least 5% w/w, at least 10% w/w, or at least 20% w/w.

23. The implant of claim 1 wherein the implant is selected from the groups consisting of bone fixation plates, intramedullary nails, hip joint implants, knee joint implants, elbow joint implants, spine implants, and devices for fracture fixation, tendon reattachment, spinal fixation, and spinal cages.

24. A method of treatment for an orthopedic application in a subject in need of treatment thereof, comprising implanting to the subject the medical implant of claim 1.

25. The implant of claim 1, wherein the mineral to polymer weight ratio in the surface composition is less than 30% of mineral to polymer weight ratio than in the body composition.

26. The implant of claim 25, wherein the mineral to polymer weight ratio in the surface composition is less than 10% of mineral to polymer weight ratio than in the body composition.

27. The implant of claim 1, wherein the surface layer comprises a surface composition with at least 10% higher polymer content than the body composition.

28. The implant of claim 27, wherein the surface layer comprises a surface composition with at least 20% higher polymer content than the body composition.

29. The implant of claim 28, wherein the surface layer comprises a surface composition with at least 30% higher polymer content than the body composition.

30. The implant of claim 29, wherein the surface layer comprises a surface composition with at least 50% higher polymer content than the body composition.

31. An implant with a body composition of mineral and polymer with a surface comprising a different composition than the implant body, wherein 10-70% w/w of the body composition comprises mineral material, wherein said material comprises 1-15% w/w calcium, wherein the body comprises an interspersed composition of mineral and polymer, and a surface layer, wherein said surface layer comprises a surface composition of at least 10% of the surface that is of a different composition than the body composition and comprises less than 4% w/w silica; wherein the body comprises more than 8% w/w silica; wherein the calcium content of the surface is 50% w/w less than the calcium content of the body composition; and wherein the surface layer comprises a surface composition with at least 10%, higher polymer content than the body composition.

* * * * *